United States Patent
Swager et al.

(10) Patent No.: US 11,047,826 B2
(45) Date of Patent: Jun. 29, 2021

(54) CHEMIRESISTIVE SENSOR AND METHODS OF SENSING

(71) Applicant: MASSACHUSETTS INSTITUTE OF TECHNOLOGY, Cambridge, MA (US)

(72) Inventors: Timothy Swager, Newton, MA (US); Vera Schroeder, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 56 days.

(21) Appl. No.: 16/354,322

(22) Filed: Mar. 15, 2019

(65) Prior Publication Data

US 2019/0285577 A1 Sep. 19, 2019

Related U.S. Application Data

(60) Provisional application No. 62/643,743, filed on Mar. 15, 2018.

(51) Int. Cl.
| | |
|---|---|
| *G01N 27/414* | (2006.01) |
| *H01L 51/05* | (2006.01) |
| *H01L 51/10* | (2006.01) |
| *H01L 51/00* | (2006.01) |

(52) U.S. Cl.
CPC ..... *G01N 27/4146* (2013.01); *G01N 27/4141* (2013.01); *H01L 51/105* (2013.01); *H01L 51/0003* (2013.01); *H01L 51/0508* (2013.01)

(58) Field of Classification Search
None
See application file for complete search history.

(56) References Cited

U.S. PATENT DOCUMENTS

| | | | |
|---|---|---|---|
| 6,537,498 B1 | 3/2003 | Lewis et al. | |
| 8,951,473 B2 * | 2/2015 | Wang | B82Y 30/00 |
| | | | 422/82.02 |
| 9,739,737 B2 | 8/2017 | Swager et al. | |
| 9,755,150 B2 | 9/2017 | Swager et al. | |
| 10,252,907 B2 | 4/2019 | Breinlinger et al. | |
| 2004/0202856 A1 * | 10/2004 | Blok | G01N 27/126 |
| | | | 428/325 |
| 2010/0323925 A1 * | 12/2010 | Gabriel | G01N 27/4146 |
| | | | 506/39 |
| 2013/0273665 A1 | 10/2013 | Swager et al. | |
| 2014/0102539 A1 | 4/2014 | Swager et al. | |
| 2015/0247832 A1 * | 9/2015 | Swager | G01N 27/127 |
| | | | 436/142 |
| 2016/0169810 A1 | 6/2016 | Swager et al. | |
| 2017/0355595 A1 | 12/2017 | Breinlinger et al. | |

FOREIGN PATENT DOCUMENTS

WO WO-2013180801 A1 * 12/2013 ............. G01N 27/12

OTHER PUBLICATIONS

B. Esser, et al.; "Selective Detection of Ethylene Gas Using Carbon Nanotube-based Devices: Utility in Determination of Fruit Ripeness", Angewandte Chemie International Edition, 51(23): p. 5752-5756, June (Year: 2012).*

(Continued)

*Primary Examiner* — J. Christopher Ball
(74) *Attorney, Agent, or Firm* — Honigman LLP

(57) ABSTRACT

A sensor can include a catalyst.

20 Claims, 20 Drawing Sheets

(56) References Cited

OTHER PUBLICATIONS

S.F. Liu, et al.; "Single-Walled Carbon Nanotube-Metalloporphyrin Chemiresistive Gas Sensor Arrays for Volatile Organic Compounds", Chemistry of Materials, 27(10): p. 3560-3563, May (Year: 2015).*

International Search Report and Written Opinion for PCT/US2019/022395 dated May 24, 2019.

* cited by examiner

Schematic of sensor catalytic mixture:[1]

X = I, Br, Cl

US 11,047,826 B2

CHEMIRESISTIVE SENSOR AND METHODS OF SENSING

PRIORITY CLAIM

This application claims priority from U.S. Provisional Patent Application No. 62/643,743, filed Mar. 15, 2018, which is incorporated by reference in its entirety.

FIELD OF THE INVENTION

The invention relates to sensors including catalysts.

BACKGROUND

Carbon monoxide is an analyte of considerable importance, particularly for safety reasons. Currently available methods for determining the concentration of carbon monoxide can suffer from high cost and impracticality of implementation in the field.

SUMMARY

In one aspect, a sensor can include a conductive region in electrical communication with at least two electrodes, the conductive region including a conductive material and a catalytic mixture that catalyzes conversion of an analyte to a product.

In another aspect, a method of sensing an analyte, can include exposing a sensor to a sample, the sensor including a conductive region in electrical communication with at least two electrodes, the conductive region including a conductive material and a catalytic mixture that catalyzes conversion of an analyte in the sample to a product, and measuring an electrical property at the electrodes.

In certain circumstances, the conductive material can include a carbon material. For example, the carbon material can include amorphous carbon, graphene, graphite, a single walled carbon nanotube, or a multiwalled carbon nanotube. In other circumstances, the conductive material can be a conductive polymer.

In certain circumstances, the analyte can be an alkene, or other volatile organic molecule. For example, the analyte can be an acrylate.

In certain circumstances, the catalytic mixture can include a catalytic metal complex.

In certain circumstances, the catalytic mixture can include a reactant that reacts with the analyte in the presence of the catalyst.

In certain circumstances, the sensor can include a selector. The selector can include a pi-radical moiety, for example, an aromatic, heteroaromatic, polyaromatic or metal complex.

In another aspect, a method of preparing a sensor can include forming a conductive region in electrical communication with at least two electrodes, the conductive region including a conductive material and a catalytic mixture that catalyzes conversion of an analyte to a product.

Other aspects, embodiments, and features will be apparent from the following description, the drawings, and the claims.

DETAILED DESCRIPTION

Figure 1A:
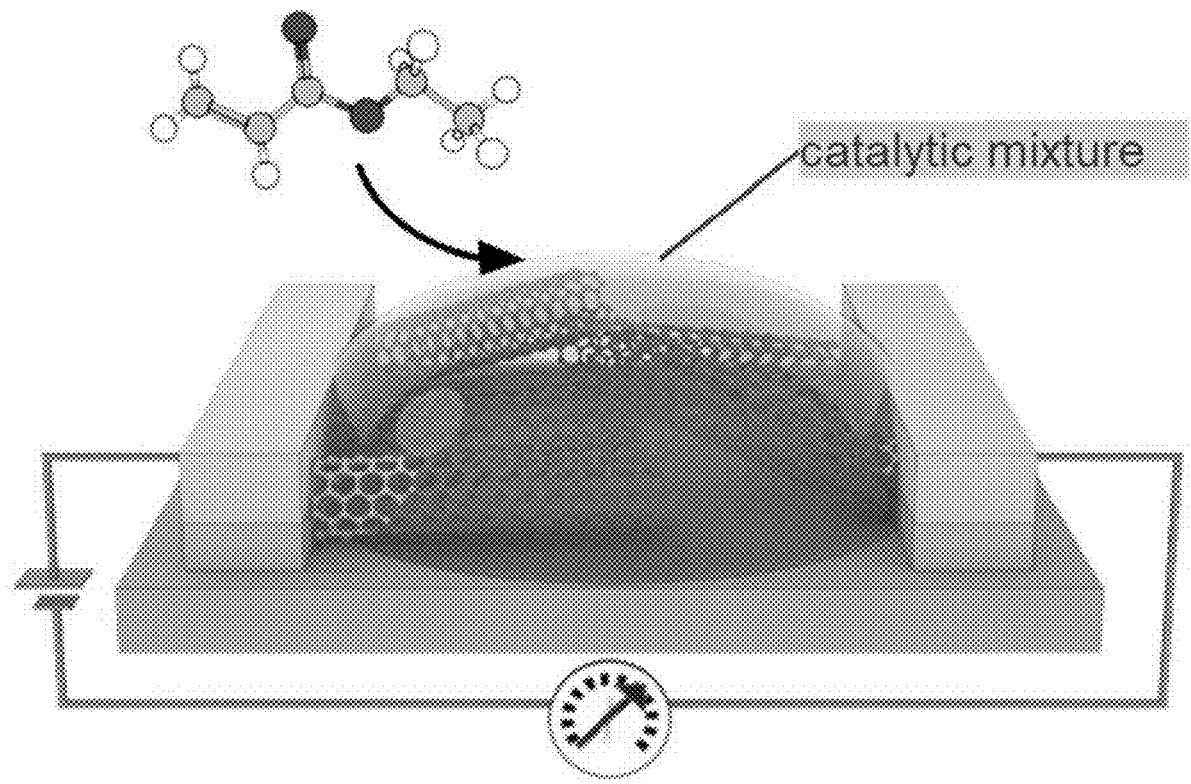
FIGS. 1A-1C depict a schematic of sensor.
Figure 1B:
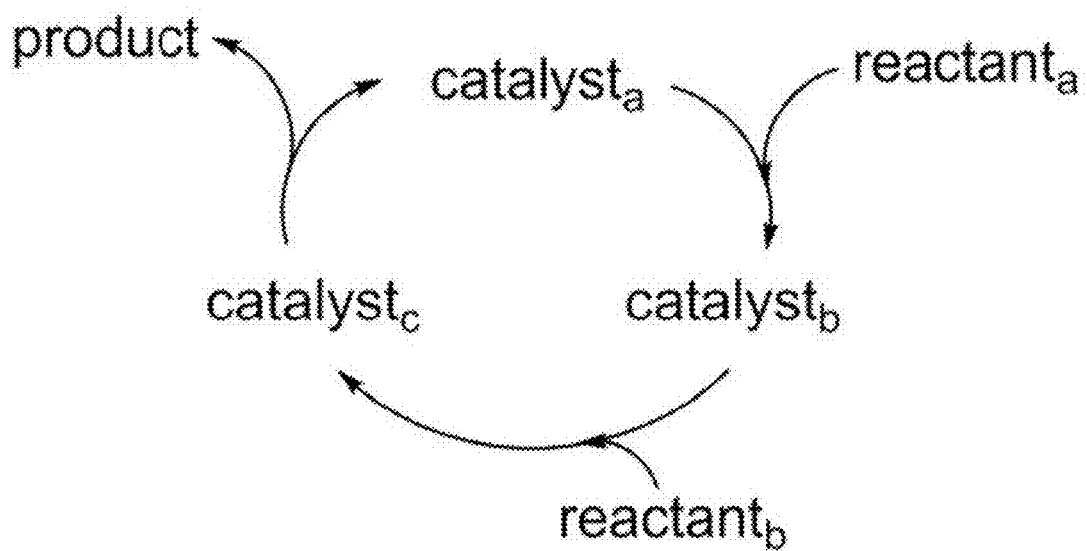
Figure 1C:
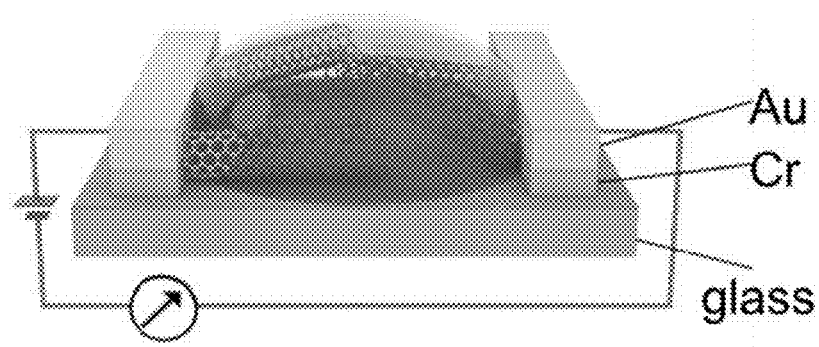
Figure 1C:
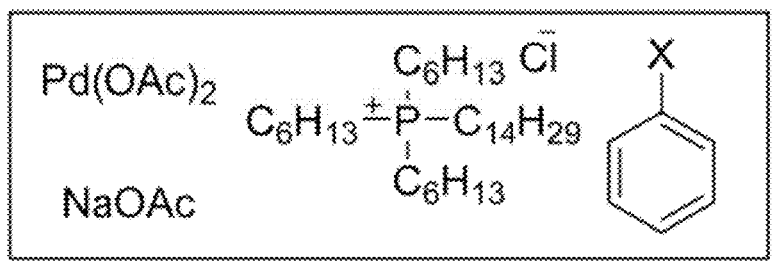

FIGS. 1A and 1C depict a sensor that can include a first electrode and a second electrode on a substrate. A conductive material can be deposited between the electrodes. A catalytic mixture can be deposited on the carbonaceous material. The catalytic mixture includes a catalyst capable of converting with a desired reactant (for example, the analyte) to a product. The catalytic mixture can include other chemical components such as other reactants, solvents or other molecules that facilitate the reaction catalyzed by the catalyst. When the catalytic mixture is exposed to the desired reactant, for example, an analyte, the composition of the catalytic mixture converts the reactant (or analyte) into a product. Because the catalytic reaction involves oxidation or reduction of the catalyst in the catalytic mixture, the electrodes can be used to detect the activity. In certain embodiments, the electrodes provide a voltage that can contribute to a cycling of the catalyst to an active or inactive state. The conductive material can be a conducting polymer, such as, for example, polyacetylene, polyaniline, polypyrrole, polythiophene, polyphenylene, polyphenylenevinylene, or other conducting complex or polymer. In other embodiments, the conductive material can be a carbon material, such as amorphous carbon, graphene, graphite, a single walled carbon nanotube, or a multiwalled carbon nanotube. The conductive material can be a combination of these materials.

The gap between electrodes can range from 0.1 mm to 10 mm. The layer thickness of the conductive material and the catalytic mixture can be between 0.1 μm to 5 μm. The molar ratio between the catalytic mixture and the conductive material can be between 5:1 and 100:1.

The catalyst can be a metal catalyst that facilitates a reaction with the analyte. For example, the catalyst can be a platinum or palladium catalyst, or other transition metal, that converts the analyte to a product. For example, the catalyst can be a palladium catalyst and the conversion can be a Heck reaction, converting an acrylate to a phenylacrylate.

The selector can include a pi-radical moiety, for example, an aromatic, heteroaromatic, polyaromatic or metal complex.

Aromatic can include a C6-C14 aromatic hydrocarbon. For example, aryl can be phenyl, napthyl, or fluorenyl.

Heteroaromatic can include a C6-C14 aromatic hydrocarbon having one or more heteroatoms, such as N, O or S. The heteroaryl can be substituted or unsubstituted. Examples of a heteroaryl include, but are not limited to, azaindole, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). In some embodiments, the heteroaryl can be dithiazinyl, furyl, imidazolyl, azaindolyl, indolyl, isoquinolinyl, isoxazolyl, oxadiazolyl (e.g., (1,3,4)-oxadiazolyl, (1,2,3)-oxadiazolyl, or (1,2,4)-oxadiazolyl), oxazolyl, pyrazinyl, pyrazolyl, pyrazyl, pyridazinyl, pyridinyl, pyrimidinyl, pyrimidyl, pyrrolyl, quinolinyl, tetrazolyl, thiazolyl, thienyl, triazinyl, (1,2,3)-triazolyl, or (1,2,4)-triazolyl. The substituent on the heteroaryl group can be amino, alkylamino, or methyleneamino.

Activating molecules or functional groups with high chemoselectivity in complex environments is a central goal of transition-metal based catalysis. Promoting strong interactions between a selected substrate and a catalytic system can also be used to create highly selective and customizable sensors and these concepts are widely recognized for enzymatic processes. We demonstrate the successful translation of organometallic reactions to sensing capability. Specifically, we have developed single-walled carbon nanotube (SWCNT) chemiresistive sensors for the highly selective detection of acrylates using conditions for the aerobic oxidative Heck reaction. The sensors mirror the catalytic processes and selectively respond to electron deficient alkenes by adapting a catalytic reaction system to modulate the doping levels in carbon nanotubes. The sensors readily detect acrylates at ppm levels in untreated air. The concepts presented here are generally applicable and can guide future sensor development based upon known catalytic processes.

Selectivity in a chemical sensor is dependent upon molecular interactions between a target molecule and the selector unit of the sensing device. The interaction can either be physical via adsorption or swelling, chemical via reaction of selector and target, or a complementary molecular recognition event levering complementary DNA interaction or receptor/guest interactions in biomolecules. See References 1-11. To expand the scope of this paradigm, we demonstrate here how a transition metal catalytic cycle developed for synthetic utility, can be used to create robust selective sensors for ethyl acrylate and similarly reactive carbon-carbon multiple bond containing molecules.

Electron rich alkenes and alkynes can detected by reactivity schemes using tetrazine functionalized SWCNT networks. See references 12 and 13. In this scheme, the tetrazine selector undergoes Diels-Alder reactions with the target extruding di-nitrogen as one of the reaction products. Upon reaction, the electron donating properties of the selector change which induces a change in the conductivity of the SWCNT-based matrix. Over the lifetime of the sensor, the tetrazine selector is consumed, which limits its long-time stability and can give dose dependent changes in sensitivity. In this work, we target electron deficient alkenes including acrylates used on very large scale in the production of polymers. We have further targeted the use of transition metal-catalyzed reactions in this process, wherein the catalyst is cycled between different oxidation states that can be used to produce changes in the conductance of a carbon nanotube network. Over the lifetime of the senor, the catalyst intermediate (selector) regenerates by completing the catalytic cycle and in the absence of the target analyte the system is in the resting state.

Our targeted acrylate analytes are preferred substrates for the oxidative, Pd-catalyzed cross-coupling of olefins with arylboronic acids as depicted in Scheme 1. The catalytic cycle involves redox cycling between palladium(0) and palladium(II) and use dioxygen as the oxidant. See References 14-17. We hypothesized that the same redox cycling could be used to promote a chemiresitive response in a chemiresistive device. There are abundant similar catalytic schemes and hence by utilizing catalytic reactions that have been optimized for synthesis, we envision a expansive opportunity for the creation of chemireisitive sensors.

Scheme 1: Aerobic oxidative Heck arylation of olefins.

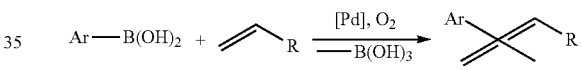

Ethyl acrylate is a toxic compound found in many industrial workplaces where it is used to fabricate acrylic resins, polymers used in paint, textiles, adhesives, or sealants. See Reference 18. Exposure to ethyl acrylate can lead to irritation of the nose, throat, and lungs. See References 19 and 20. At concentrations above 25 ppm it can induce drowsiness, dizziness, fatigue, headache, nausea, difficulty in breathing, and even convulsions. See Reference 18. Furthermore, exposure to ethyl acrylate is linked to increased levels of cancer in animal trials. See References 21 and 22. Current technologies for the detection of ethyl acrylate consist of the collection of air samples at the point of exposure and then remote analysis by gas chromatography. See Reference 18. This classical laboratory scheme precludes real-time monitoring of ethyl acrylate and other related carcinogenic compounds. Light weight chemiresistive sensors can allow for real time monitoring or ideally wearable sensors that can be read wirelessly. See References 23 and 24.

Figure 2A:
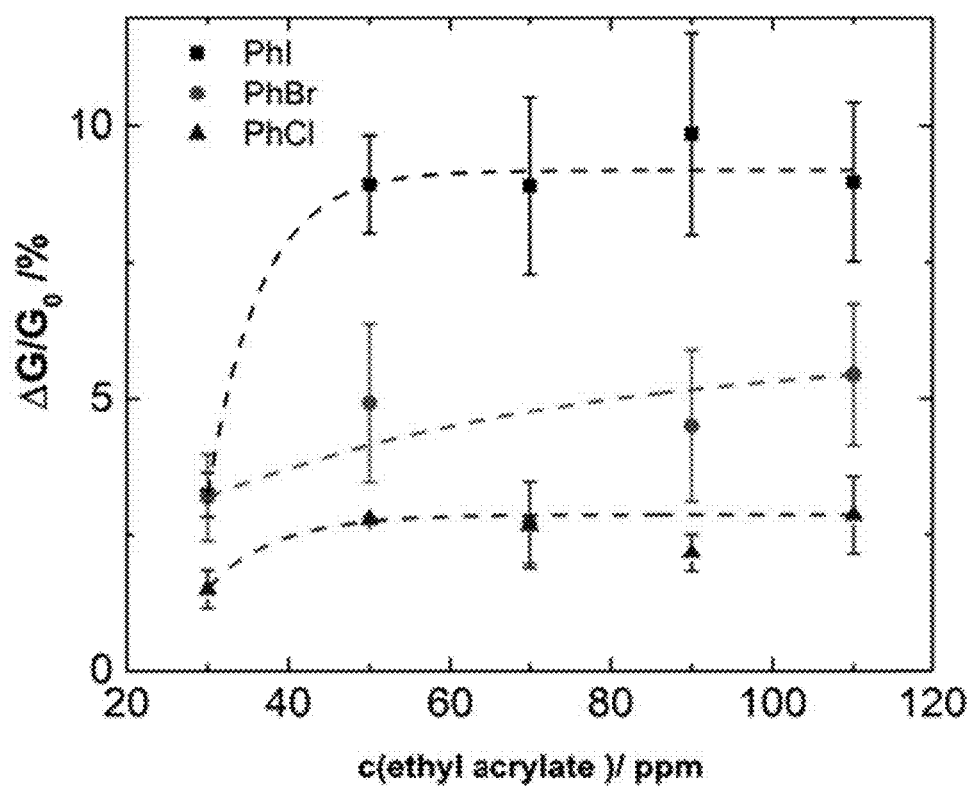
FIG. 2A depicts a response of a sensor.
Figure 2B:
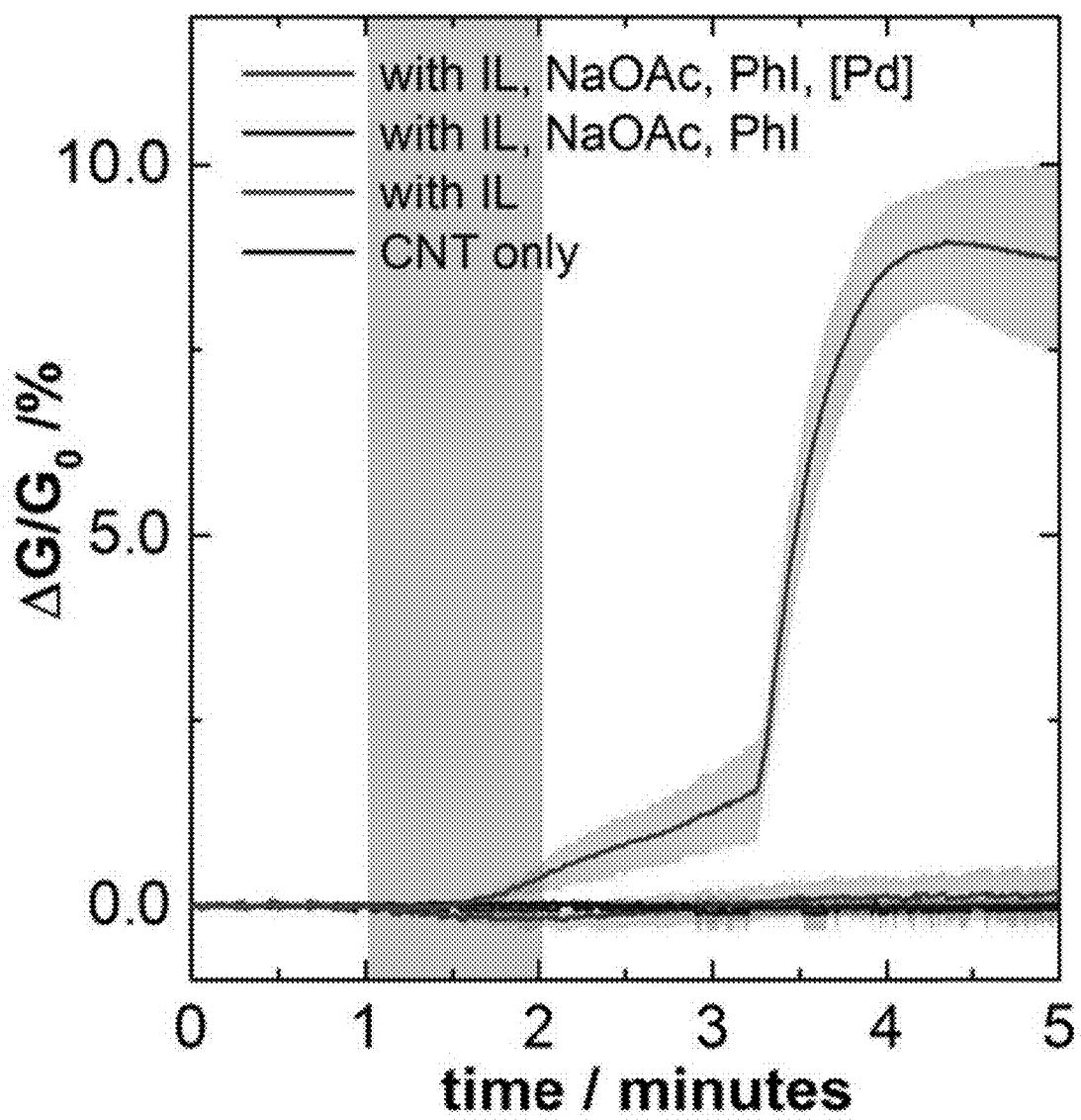
FIG. 2B depicts a response of a sensor.

Our initial proof-of-principle sensing experiments employed $Pd(OAc)_2$, NaOAc, trihexyl(tetradecyl)phosphonium chloride, and iodo-, bromo- or chlorobenzene in a ratio of 0.04:1.5:10:1.0. See Reference 25. Chemiresistive sensors make use of a random nano-wire matrix of single-walled carbon nanotubes (SWCNTs) that are made to interact with the selectors. This SWCNT matrix interconnects two gold electrodes on an insulating glass substrate and the sensor signal is the changes in the normalized current between the electrodes with an applied constant voltage. We represent the signal from the sensor device as ($\Delta G/G_0$), wherein $\Delta G$ is the change conductance (current) and $G_0$ is the baseline response in the absence of analyte. FIG. 2A shows the response of these solid phase devices to ethyl acrylate with different catalytic formulations. Referring to FIG. 2A, a proof-of-principle sensor for ethyl acrylate demonstrates a response of SWCNT-sensor using a mixture of Pd(OAc)$_2$, NaOAc, trihexyl(tetradecyl)phosphonium chloride, and iodo-, bromo- or chlorobenzene as the co-selector towards different concentration of ethyl acrylate in N$_2$. The dotted lines are used to guide visualization. Upon contact with ethyl acrylate vapor the current through the device decreases dramatically even at concentrations as low as 50.0 ppm. Control experiments under the same exposure conditions, using devices with pure SWCNTs or SWCNTs mixed with an ionic liquid, NaOAc, and/or halobenzene but lacking the palladium catalyst precursor displayed no observable response (FIG. 2B). Referring to FIG. 2B, additional controls for proof-of-principle system are shown. Average changes in the conductance and standard deviations (N≥6 sensors) in response to 1 min exposures of 50 ppm ethyl acrylate in N$_2$ (shaded area) for sensors with CNT-only (black curve), sensors with the IL, trihexyl(tetradecyl)phosphonium chloride (red curve), sensors missing the Pd-source, Pd(OAc)$_2$ (green curve), and sensors with the complete catalytic mixture containing Pd(OAc)$_2$, NaOAc, trihexyl(tetradecyl)phosphonium chloride, and iodobenzene (green curve).

For example, chemiresistive sensors can be based on SWCNTs functionalized with a mixture of [Pd], base, ionic liquid, and C-coupling partner (PhX). SWCNT matrix connects two Au electrodes; the sensor signal is the normalized change in electrical conductance (ΔG/G0) upon exposure of the sensor to an analyte. Upon contact with ethyl acrylate vapor the current through the device with catalytic mixture (green curve) increases dramatically even at concentrations as low as 50.0 ppm.

Figure 2C:
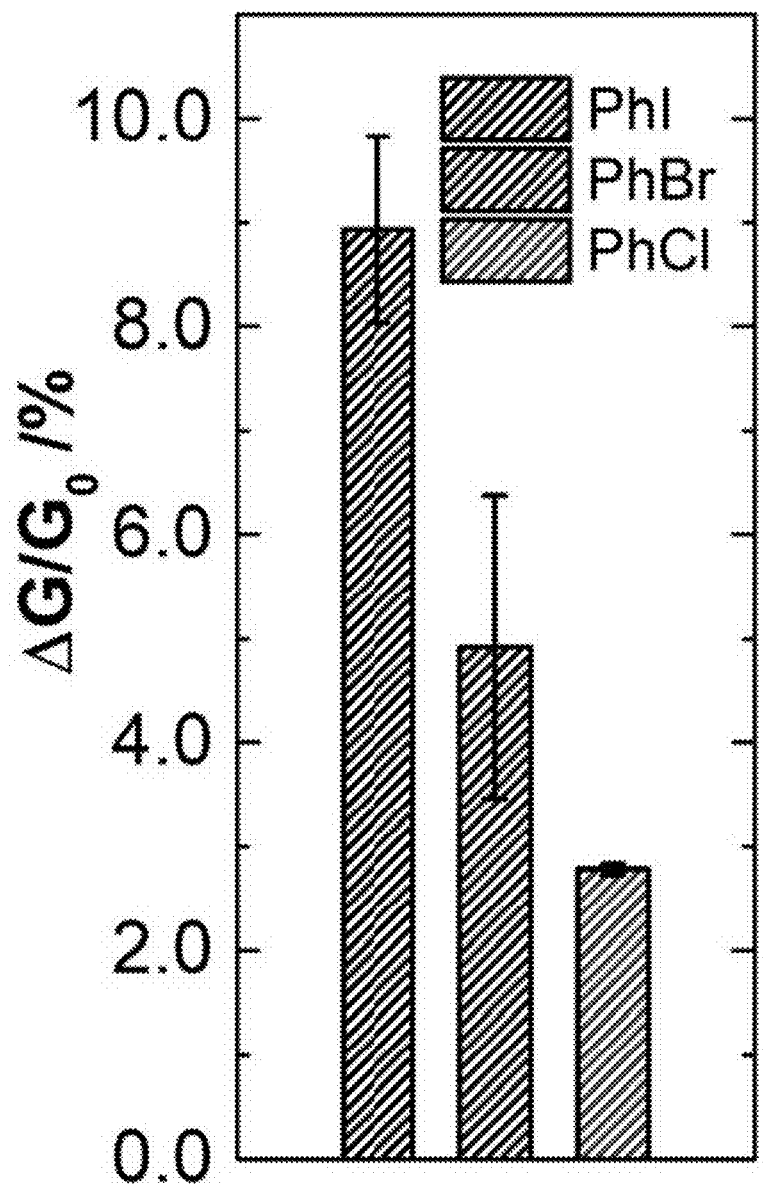
FIG. 2C depicts a response of a sensor.

The magnitude of the response of the device towards exposure of ethyl acrylate follows the expected reactivity trend iodobenzene>bromobenzene>chlorobenzene (FIG. 2C) that is observed for the same catalytic reaction in solution. See References 25 and 26. However, the response of the detector does not scale linearly with concentration of ethyl acrylate. We suspect that the inhomogeneity of the system is at least partially to blame for the non-linear behavior. Additionally, in ligand-free Heck reactions the catalytic species is ill-defined and is often assumed to be colloidal palladium. See Reference 26.

Figure 3:
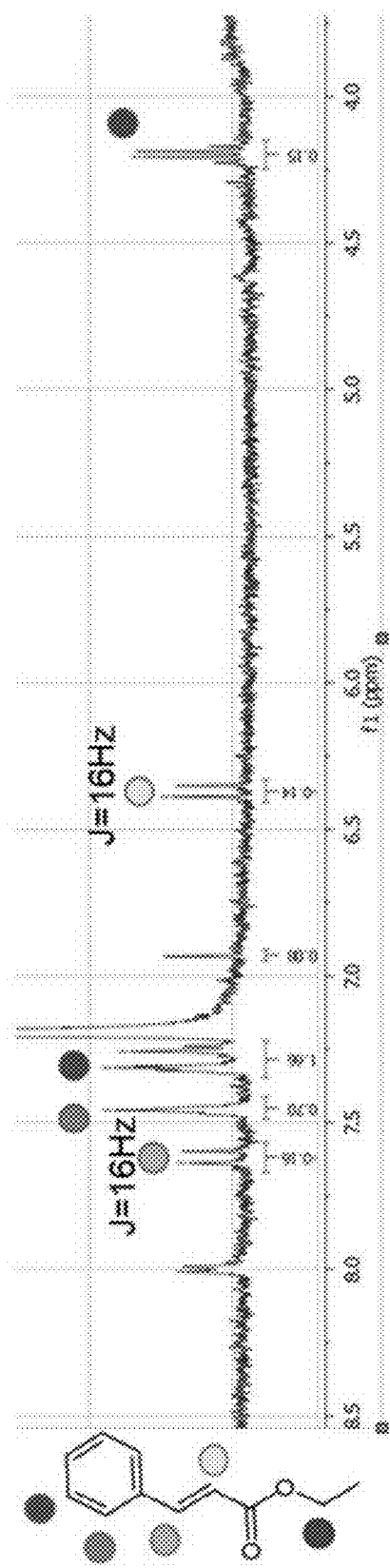
FIG. 3 depicts spectral properties of a product.

To support our working hypothesis that the sensing signal is produced by the coupling reaction of ethyl acrylate and halobenzene we attempted to isolate the reaction products from our sensing device. The device was washed with chloroform after a 14 h exposure to ethyl acrylate (100 ppm) to isolate the reaction product. Proton NMR of the extracted material reveals that ethyl cinnamate is produced (FIG. 3), supporting our hypothesis that the catalytic reaction can be performed on the sensing device. Referring to FIG. 3, $^1$H-NMR spectrum of reaction product of Heck reaction between iodo-benzene and ethyl acrylate in CDCl$_3$ isolated from sensing device after 14 h exposure to 100 ppm ethyl acrylate. Literature reference: (400 MHz, CDCl$_3$): δ 1.34 (3H, t, J=7.1 Hz, CH3), 4.27 (2H, q, J=7.1 Hz, OCH2), 6.44 (1H, d, J=16.0, EtOCCH=), 7.37-7.39 (3H, m, Ar—H), 7.51-7.52 (2H, m, Ar—H), 7.69 (1H, d, J=16.0,ArCH=).[27]

Building upon these successful proof-of-principle investigations, we targeted a homogeneous system with a ligand-stabilized active catalytic species. In particular, we decided to adapt the aerobic oxidative Heck couplings. See Reference 28. An advantage is that the carrier gas (air) acts as the oxidant, which will be present in most sensing use cases. The catalytic mixture also contains [Pd(CH$_3$CN)$_4$](BF$_4$)$_2$ as the palladium source, 4,5-diazafluorenone as the ligand and phenylboronic acid as the coupling partner (ratio 0.05:0.05: 1).

Figures 4A, 4B:
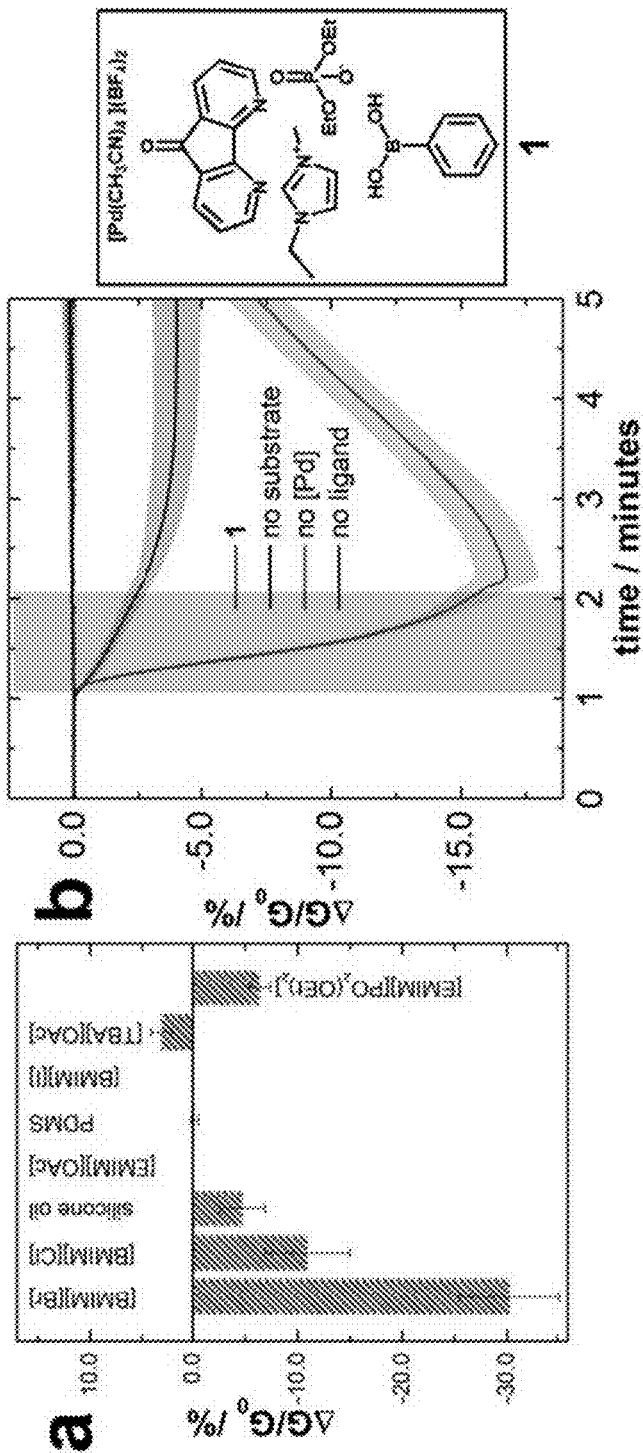
FIGS. 4A-4E depict properties of a sensor.
Figure 4C:
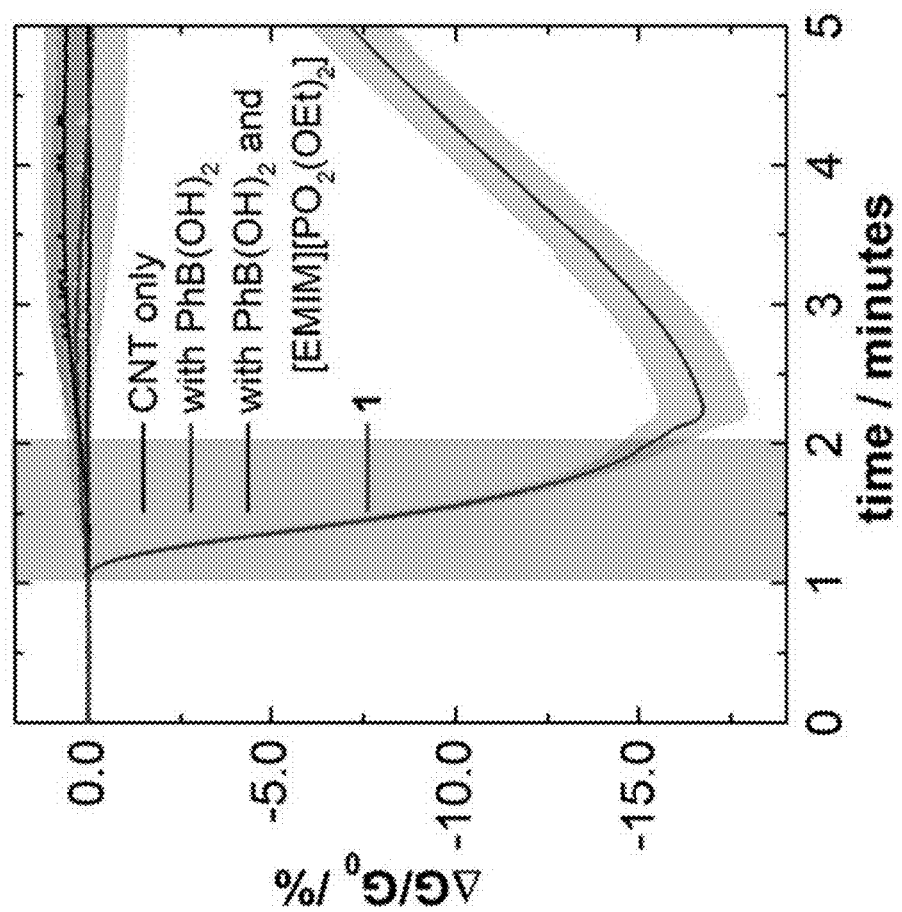
Figure 4D:
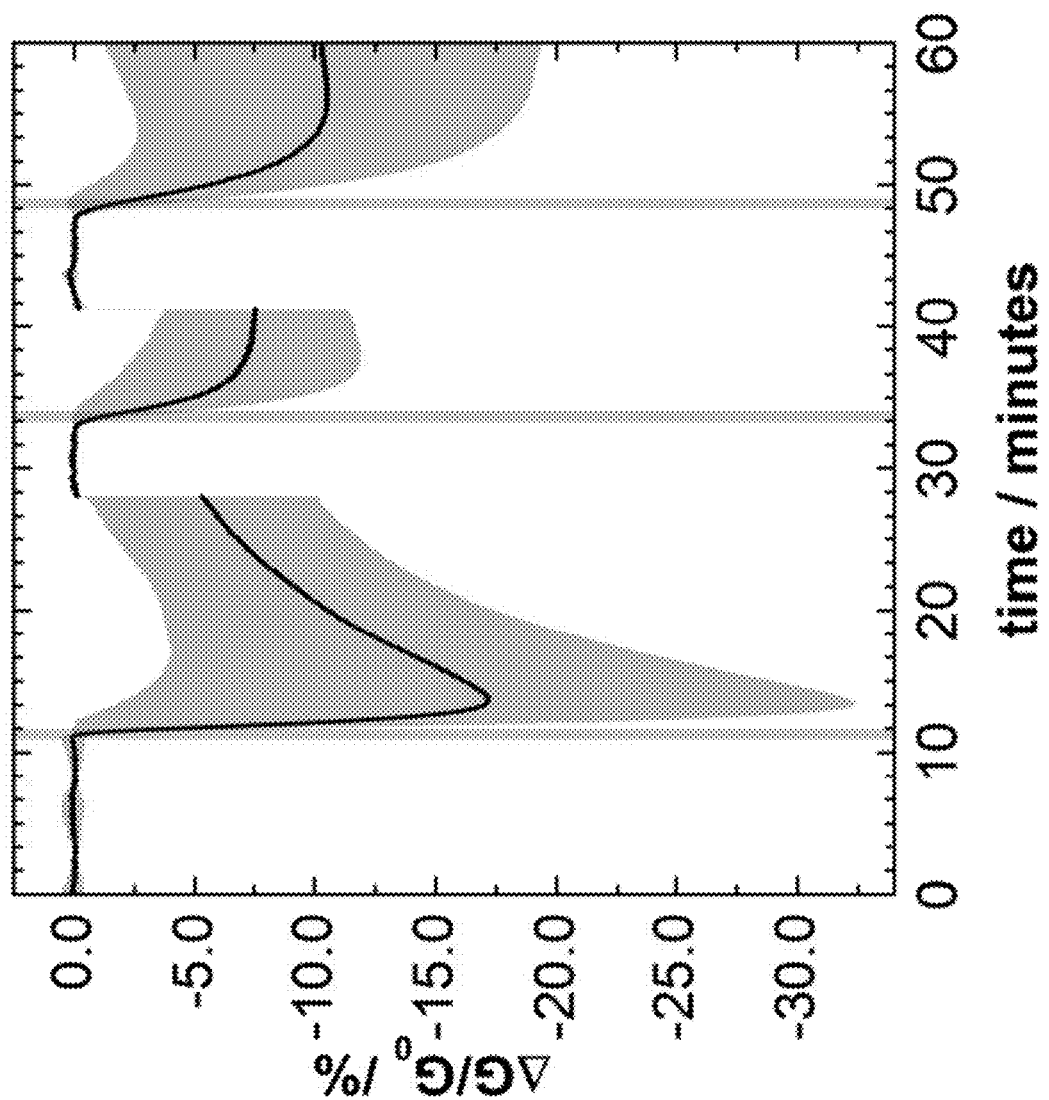
Figure 4E:
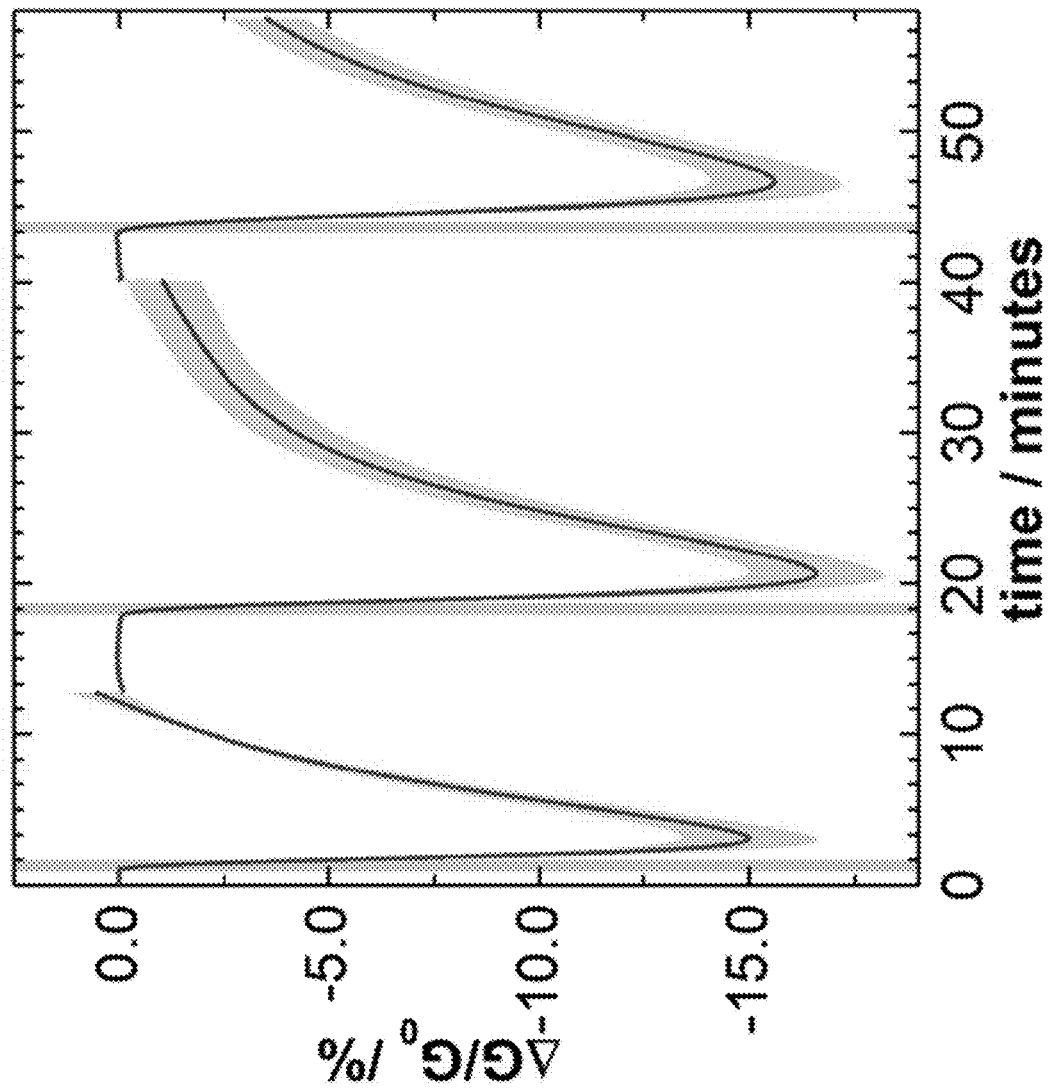

In developing a sensor that utilizes this catalytic reaction in a solution environment, we investigated a number solvents that could persist over prolonged sensing experiments. FIGS. 4A-4C show the response of sensors with eight different solvents; ionic liquids, silicone oil, and low viscosity PDMS. Among the tested solvents, 1-butyl-3-methylimidazolium bromide ([BMIM][Br]) gave the strongest response albeit with limited reversibility. No response was observed from the Heck reaction when [BMIM][I] or [EMIM][OAc] were used as the solvent The reaction in [EMIM][PO$_2$(OEt$_2$)] showed a moderate response, but had the advantage of providing full reversibility. With the optimized reaction conditions in hand, we investigated the sensing mechanism of the sensor. Referring to FIGS. 4A-4E: (a) Sensor response of device containing with different solvents using [Pd(CH$_3$CN)$_4$](BF$_4$)$_2$, 4,5-diazafluorenone, and phenylboronic (ratio 0.05:0.1:1) towards 50.0 ppm ethyl acrylate diluted in air (relative humidity=46%). (b) Average changes in the conductance and standard deviations (N≥6 sensors) in response to 1 min exposures (shaded area) for sensors missing the boronic acid coupling partner (black curve), sensor missing the Pd source (red curve), sensors missing the ligand (green curve), and the complete catalytic mixture 1 (green curve) sensors and insert with components of catalytic mixture 1.

To support our hypothesis that the catalytic reaction is causing the sensor response, we performed several control experiments. FIG. 4B shows the device responses with different functionalizations in response to 60 s exposures of 50 ppm ethyl acrylate in air. Control experiments with pristine SWCNTs (FIG. 4C), or with ionic liquid only (FIG. 4C) showed negligible responses. Sensors missing vital components of the catalytic system—the boronic acid coupling partner (black curve), or the palladium source (red curve)—also show no response towards ethyl acrylate exposure, thereby supporting our hypothesis that the catalytic reaction is responsible for the chemiresisitive behavior. Referring to FIG. 4C, additional controls for proof-of-principle system are shown. Average changes in the conductance and standard deviations (N≥6 sensors) in response to 1 min exposures of 50 ppm ethyl acrylate in air (shaded area) for sensors with CNT-only (black curve), sensors with phenylboronic acid (red curve), sensors with phenylboronic acid and [EMIM][PO$_2$(OEt)$_2$] (green curve), and sensors with the complete catalytic mixture 1 (green curve). Additionally, the direction of the response to lower conductivity is consistent with the sensing mechanism. In the absence of the olefin coupling partner (ethyl acrylate), the resting state of the catalytic cycle is the arylpalladium(II) intermediate. Upon reaction with olefin a certain number of palladium centers will transiently exist in a (formally) Pd(0) state. SWCNTs are p-doped by physisorbed oxygen[29,30] and charge transfer to the Pd(0) species is expected to deplete these charge carriers, which will proportionately reduce the conductance.

We note that:

Improve reversibility and stability: homogeneous system with ligand-stabilized active catalytic species; aerobic oxidative Heck couplings based on reported conditions by Izawa et al. Angew. Chemie Int. Ed. 2013, 52 (13), 3672, incorporated by reference in its entirety.

Investigate influence of IL solvents to produce reversible, stable sensors. [EMIM][PO₂(OEt₂)] showed only moderate response, but had advantage of providing good reversibility. All further sensors contain [EMIM][PO₂(OEt₂)] as a solvent.

Reversibility: Under solvent-free conditions, the sensing response is semi-reversible and repeated exposure to the same concentration leads to decreasing responses. Sensors containing [EMIM][PO2(OEt2)] have reversible responses, that do not decrease in magnitude for several consecutive exposures Control Experiments: Sensors missing vital components of the catalytic system—the boronic acid coupling partner (black curve), or [Pd] (red curve)—show no response towards ethyl acrylate exposure.

Sensors containing [Pd] and boronic acid coupling partner—but lacking the ligand—showed modest and dosimetric response indicating irreversibility over the experimental time frame.

Response increased significantly with introduction of ligand (4,5-diazafluorenone). Increase of the signal likely reflects the improved efficiency of the catalytic reaction.

Sensors containing the palladium precursor and boronic coupling partner—but lacking the ligand—showed a modest and dosimetric response indicating irreversibility over the experimental time frame (blue curve, −4.2±0.77%). The irreversibility of the response is consistent with previous reports of formation of unreactive Pd-black in ligand-free palladium reactions.[31,32] Dosimeters can be attractive in situations wherein cumulative exposures are of interest and the sensor is only read in its initial and final states. The response increased significantly with the introduction of the ligand 4,5-diazafluorenone (green curve, —16.2±1.0%). The increase of the signal likely reflects the improved efficiency of the catalytic reaction.

Figures 5A, 5B, 5C:
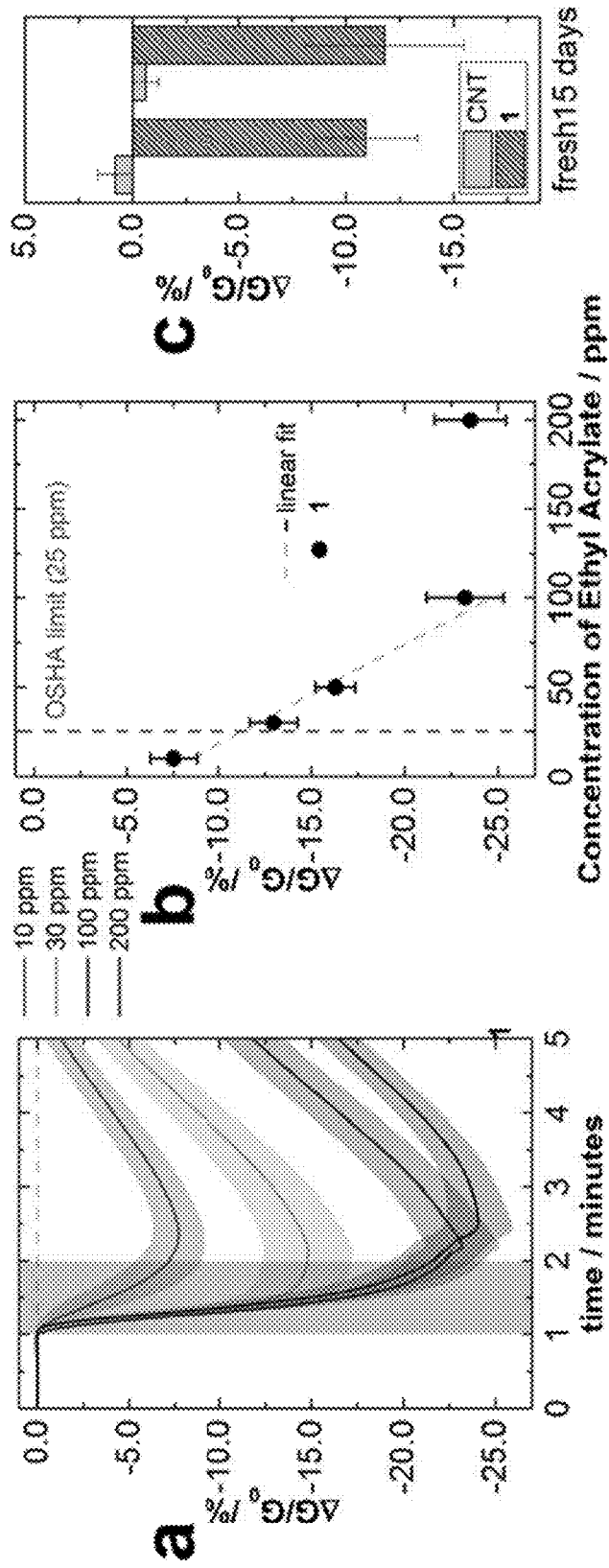
FIGS. 5A-5C depict a response of a sensor.

Referring to FIGS. 5A-5C: (a-b) Response of 1-sensors towards different concentrations of ethyl acrylate in air. (c) Reponses of device towards 50 ppm ethyl acrylate (shaded area) freshly prepared and after storage on benchtop for two weeks. To evaluate the real-world applicability of our sensors, we have investigated sensitivity, stability, and selectivity. FIGS. 5A-5B show the response to various concentrations of ethyl acrylate. The sensor responds linearly to concentrations between 10 and 100 ppm ethyl acrylate in air. We observe a clear signal for a 10 ppm 1 min exposure of ethyl acrylate (FIG. 5A), which is well within the range of OSHA's exposure limit of 25 ppm for 8 hours.[33] FIG. 5C compares the response of a device immediately after fabrication and after storage on the laboratory benchtop for two weeks. We observed no degradation of the sensor performance over this period.

FIGS. 6A-6D show the response of the device to commonly found volatile organic compounds (VOCs) that are not substrates in the Heck reaction. Neither ligating nor non-ligating VOCs elicit significant responses from a sensor functionalized with mixture 1, indicating that the sensing mechanism is not the result of ligation of the Pd source or a simple change of the solution characteristics.

Figure 6A:
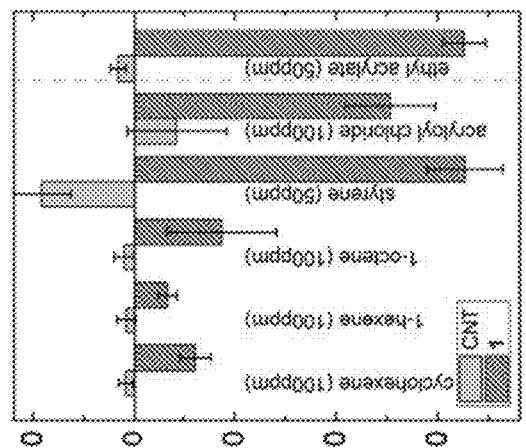
FIGS. 6A-6D depict properties of a sensor.
Figure 6B:
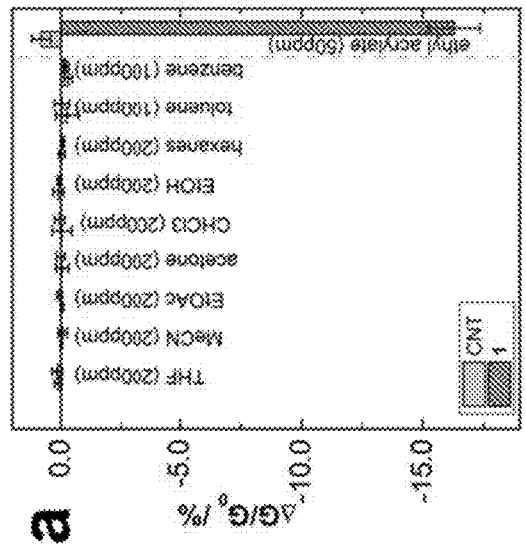
Figure 6C:
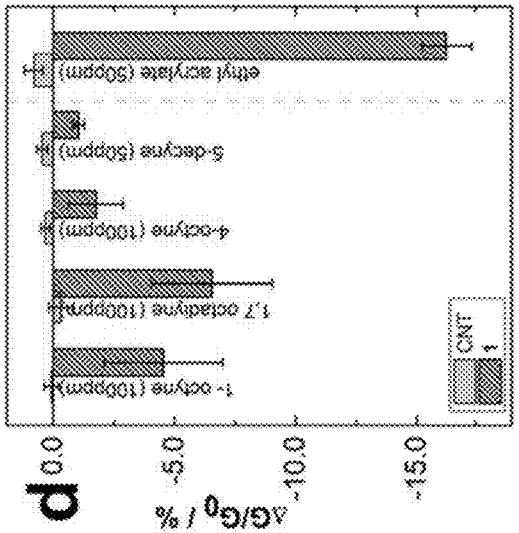
Figure 6D:
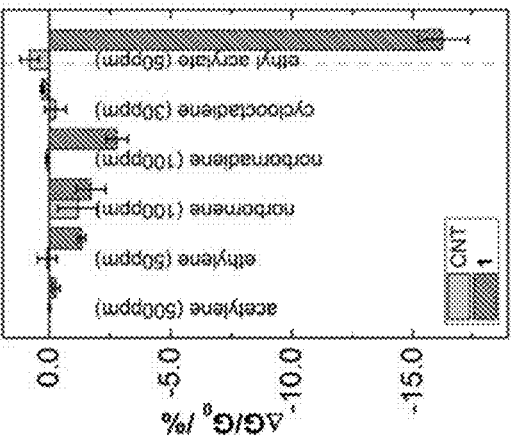

The response of our sensor follows the general reactivity trends observed for the Heck reaction. Activated alkenes (styrene, acryloyl chloride, ethyl acrylate, FIG. 6B) have higher responses than simple linear or cyclic alkene compounds (cyclohexene, 1-hexene, 1-octene, FIG. 6B). Strained cyclic alkenes like norbornene, norbornadiene, and cyclooctadiene are challenging compounds for Heck reactions and also give lower responses in our sensing experiments (FIG. 6C). See References 34-37. Additionally, substrates for Heck alkynation (copper-free Sonogashira) can be used successfully FIG. 6D. See Reference 38. Accordingly, terminal alkynes (1-octyne, 1,7 octadiyne) are more reactive than the tested internal alkyne (4-octyne, 5-decyne). Referring to FIGS. 6A-6D: Sensor response of device towards different classes of molecules: (a) volatile organic compounds, (b) simple and activated alkenes, (c) strained cyclic alkenes and small gaseous analytes, (d) and alkynes.

We note that:
Sensor response follows the general reactivity trends observed for the Heck reaction
Activated alkenes have higher responses than simple linear or cyclic alkene compounds, strained cyclic alkenes are challenging compounds for Heck reactions and also give lower responses in our sensing experiments
Substrates for Heck alkynation can be used successfully and terminal alkynes result in higher responses than internal alkynes.

Figure 7:
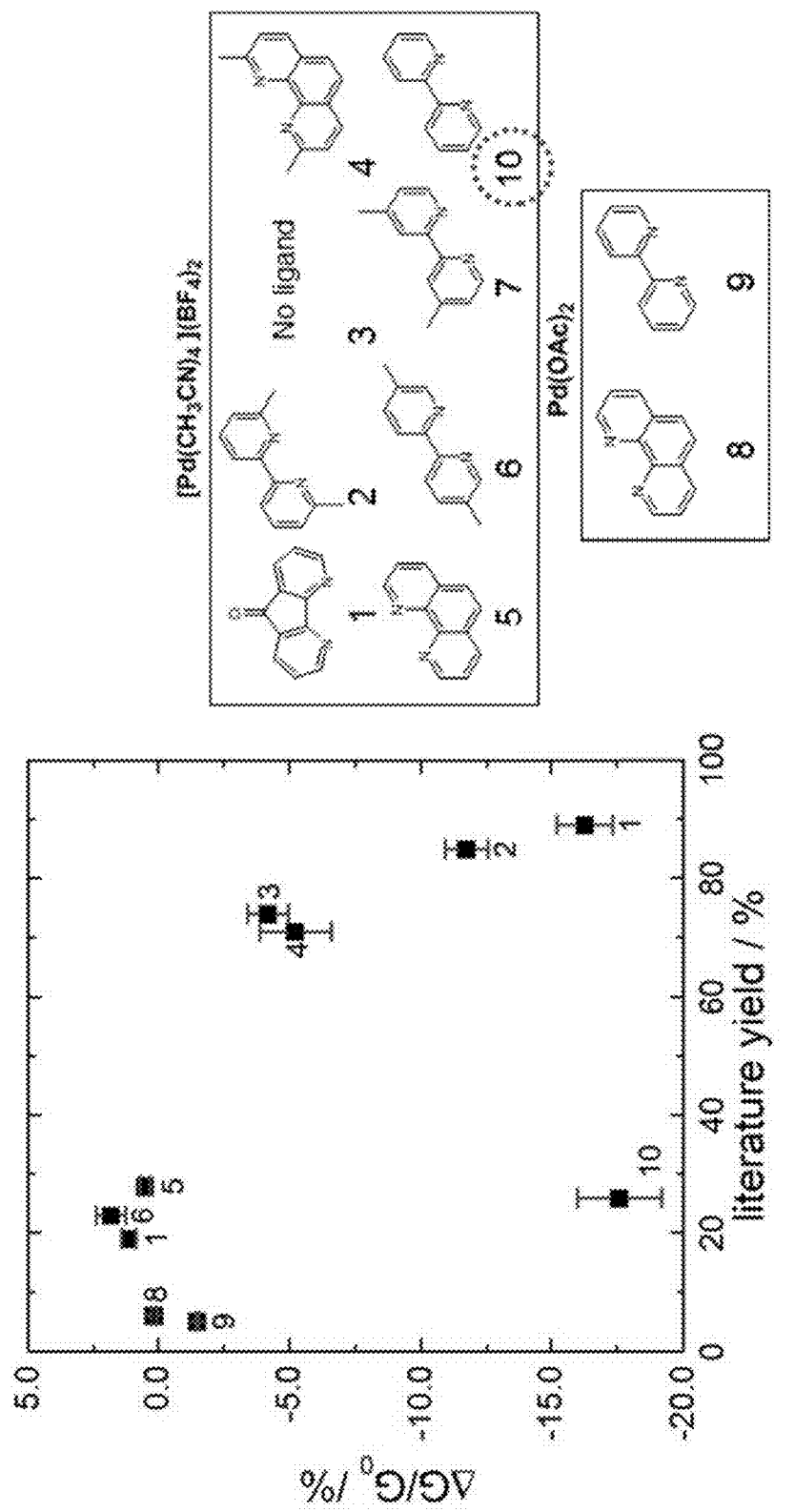
FIG. 7 depicts properties of a sensor.

Most C═C containing substrates that are traditionally used in Heck reactions have relatively low vapor pressures, and because of differences in the portioning of vapors to the catalyst solutions coating our SWCNT network, we were not able to correlate the response of our gas sensors with the literature reaction yields. As an alternative, we correlated the response of our chemiresisitive devices as a function of the nitrogen-containing ligands wherein all other conditions remain unchanged (FIG. 7). In general, the ligands that were reported to have higher reaction yields also performed better in our sensing experiments,[17,28] with a notable exception of the combination of 2,2'-bipyridine/Pd(OAc)₂ (entry 10) which only leads to moderate reaction yields but gives a very high sensing response. See References 17 and 28. Referring to FIG. 7: Sensor response of devices containing different ligands and palladium sources compared to published reaction yields: (1) 4,5 diazaflourenone/[Pd(CH₃CN)₄](BF₄)₂, (2) 4,4'-dimethyl-2,2'-dipyridyl/[Pd(CH₃CN)₄](BF₄)₂, (3) no ligand/[Pd(CH₃CN)₄](BF₄)₂, (4) 2,9-dimethyl-1,10-phenanthroline/[Pd(CH₃CN)₄](BF₄)₂, (5) phenanthroline/[Pd(CH₃CN)₄](BF₄)₂, (6) 5,5'-dimethyl-2,2'-dipyridyl/[Pd(CH₃CN)₄](BF₄)₂, (7) 6,6'-dimethyl-2,2'-dipyridyl/[Pd(CH₃CN)₄](BF₄)₂, (8) 2,2'-bipyridine/[Pd(CH₃CN)₄](BF₄)₂, (9) phenanthroline/Pd(OAc)₂, (10) 2,2'-bipyridine/Pd(OAc)₂.

We note that:
Most C═C containing substrates used in Heck reactions have very low vapor pressure, making gas sensing challenging
Alternatively: correlated response of chemiresistive devices as a function of the nitrogen-containing ligands wherein all other conditions remain unchanged
In general, ligands that were reported to have higher reaction yields also performed better in sensing experiments, with a notable exception of the combination of 2,2'-bipyridine/Pd(OAc)₂ (entry 10).
Potential to use gas sensor as a tool to probe conditions of catalytic reaction We have established direct translation of catalytic organometallic reaction conditions to chemiresitive detection of gaseous analytes. This approach can be used to greatly expand the scope of SWCNT sensors for the detection of harmful compounds by leveraging the massive investment in the development of selective catalytic reactions. Our sensors display outstanding selectivity to molecules that undergo aerobic Heck reactions, at sensitivities well under OSHA limits. We are actively seeking to adapt other catalytic processes to create selective, robust, and sensitive sensors for other groups of analytes.

The analyte can be any reactive alkenes, for example, those used in plastics, paint, and adhesives production. The catalyst can be a catalyst that facilitates reaction of the alkene. The sensor can be a stationary sensor or a wearable wireless badge. In some embodiments, the sensor can include additional electrode structures to provide a gate voltage across the conductive material.

EXAMPLES

Experimental Methods
Materials and Instrumentation

SWCNTs used in this work were purified SWCNTs with (6,5) chirality with ≥90% carbon basis (≥99% as carbon nanotubes), 0.78 nm average diameter purchased from Aldrich. Commercially available solvents—dichloromethane (DCM), 1,2-dichlorobenzene (o-DCB), acetone, tetrahydrofuran <0.025% butylated hydroxytoluene as inhibitor, isopropyl alcohol—were purchased from Sigma-Aldrich and used as received. Ethylene and acetylene were purchased from Airgas (Airgas, Dorchester, Mass.). All other chemicals were purchased from Sigma Aldrich and used without further purification. NMR spectra were recorded on Bruker Avance-400 spectrometers.

Preparation of Reaction Mixture 1

Phenylboronic acid (0.1 mmol, 12.19 mg) and 4,5 diazafluorenone (0.005 mmol, 0.910 mg) were added to a centrifuge tube and covered with 30 mg of [emim][$PO_4$]. The mixture was sonicated until the mixture was homogenous (5 min). Then tetrakis(acetonitrile) Pd(II) tetrafluoroborate (0.005 mmol, 2.22 mg) and 30 µl of NMP were added to the tube and followed by 1 min of sonication. The resulting orange mixture was used immediately after preparation.

Fabrication of Sensing Substrate

Sensors were prepared on a 25 mm×75 mm×1 mm glass substrate with gold electrodes, which was cleaned by sonication in hexanes, acetone, and isopropanol for 10 min each. The gold electrodes (100 nm thickness) were deposited on the surface of the glass slide through a stainless steel shadow mask using a Thermal Evaporator (Angstrom Engineering, Kitchener, Ontario, Canada) under pressure of 1-4×10-5 Torr and a rate of evaporation of 1-2 A/s.

Fabrication of Chemiresistive Sensor

In a typical device, the sensors were prepared by two-step deposition of SWCNTs via drop-casting and subsequent functionalization. Pristine SWCNTs were suspended in o-DCB at the concentration of 0.25 mg mL$^{-1}$ and drop-casted onto the patterned substrates between the source/drain electrodes using a micropipette. Each substrate contained 16 identical channels. The solvent was removed in vacuo. The drop-casting was repeated until the resistance across the electrodes reached a resistance of 1-3 kΩ as measured by a multimeter. Subsequently, the substrates were covered with 1 µl of a mixture of 1.

Gas Detection Measurement

Gas detection measurements were performed by placing the sensors into a custom built PTFE enclosure with a small gas inlet and outlet. Device test clip (3M) provided the electrical contacts between the source/drain electrodes and the gate. A PalmSens EmStat potentiostat equipped with a MUX16 multiplexer (Palm Instruments BV, The Netherlands, http://www.palmsens.com/) was used to apply the source-drain voltage (0.100 V) and measure the conductance across the source/drain electrodes. The data acquisition was done using PSTrace 4.8 software provided by Palm Instruments. The analyte gas and the carrier gas ($N_2$ or air) were delivered to the enclosure using rubber tubing through the inlet and outlet ports of the enclosure. Analyte gases were generated using a KIN-TEK FlexStream gas-generator (Kin-Tek Laboratories, La Marque, Tex.) or (in case of gaseous analytes) delivered using two digital mass flow controllers (MFCs) purchased from Alicat Scientific (Alicat Scientific, Tucson, Ariz).

1. Additional Control Experiments
Proof-of-Principle Sensing System

The proof-of-principle catalytic mixture containing Pd(OAc)$_2$, NaOAc, trihexyl(tetradecyl)phosphonium chloride, and iodobenzene in a ratio of 0.04:1.5:10:1.0 shows a strong albeit delayed response. Due to the time delay between exposure and response, the non-linear relationship between concentration and response (FIG. 2A), and the irreversibility of the system, we decided to investigate catalytic systems containing well-defined molecular catalysts. See Reference 25a.

Figure 8:
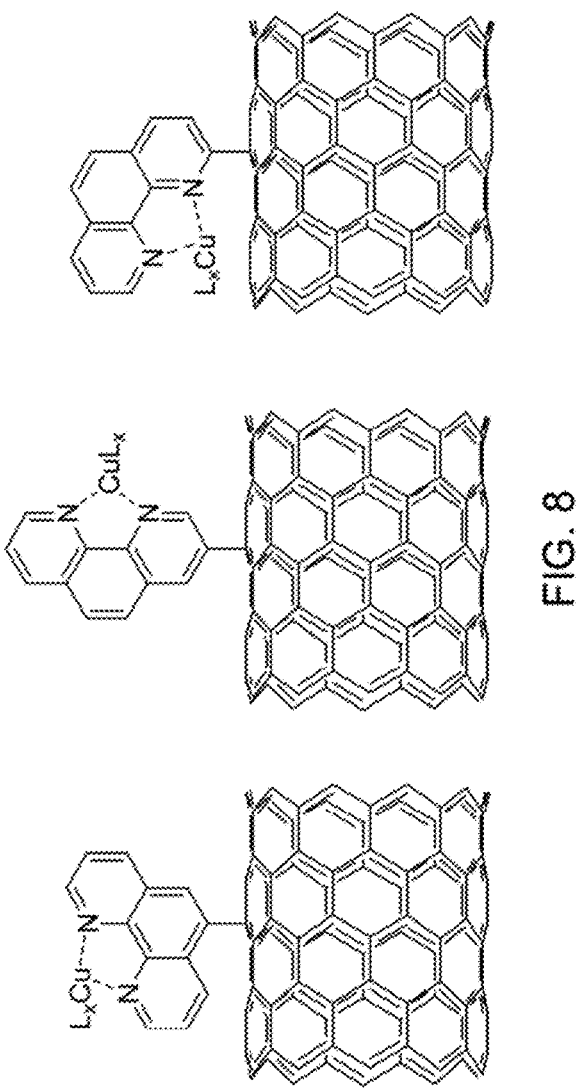
FIG. 8 depicts a sensor.

Building upon the success of the carbon monoxide SWCNT-FET devices, we aim to use phenanthroline-functionalized SWCNTs ligated to copper to broaden the scope of our FET-based sensors with voltage-activated sensitivity, FIG. 8, which depicts SWCNTs functionalized with copper phenanthroline complexes. This system will be used for voltage modulated sensors for CO and NO. The goal of this route is to further develop the tunability of our sensors using applied gate voltage as the switch. Previously, we have shown that the sensitivity of the sensors toward carbon monoxide can be improved with the application of negative gate voltage. Now, we aimed to create a multimodal sensor that can detect different analytes at different gate voltages. Specifically, the gate voltage will tune the selectivity of the sensors.

Figure 9:
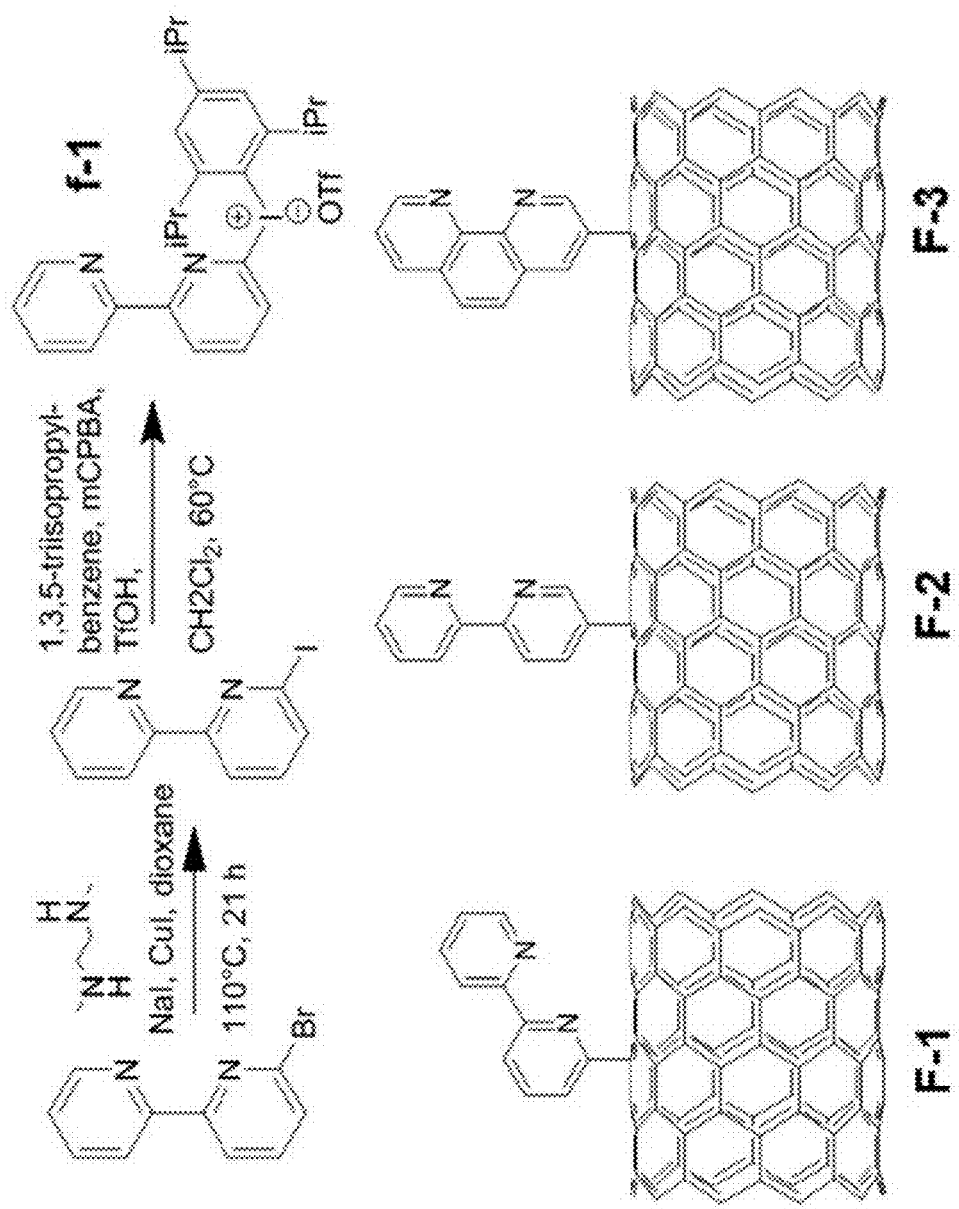
FIG. 9 depicts a sensor.

We first investigated the use of copper ions such that we can modulate between $Cu^1$ and $Cu^{11}$ to tune the selectivity of the sensors. To incorporate copper into our system comprising SWCNTs, we started by covalently functionalized SWCNTs with new ligands containing either bipyridine or phenanthroline complexes. These complexes are more suitable to chelate copper ions than the pyridyl ligand used in the previous study. FIG. 9 shows the synthesis of the 2-bipyridine iodonium salt (f-1) and the resulting covalently functionalized SWCNTs (F-1) by our previously reported method.[9] Similarly, the 3-bipyridine and 3-phenanthroline iodonium salts were synthesized and covalently functionalized onto SWCNTs, resulting in F-2 and F-3. The resulting functionalized SWCNTs were confirmed via ultraviolet-visible-near infrared spectroscopy (UV-vis-NIR), Raman spectroscopy, thermogravimetric analysis (TGA), and x-ray photoelectron spectroscopy (XPS).

Figure 10:
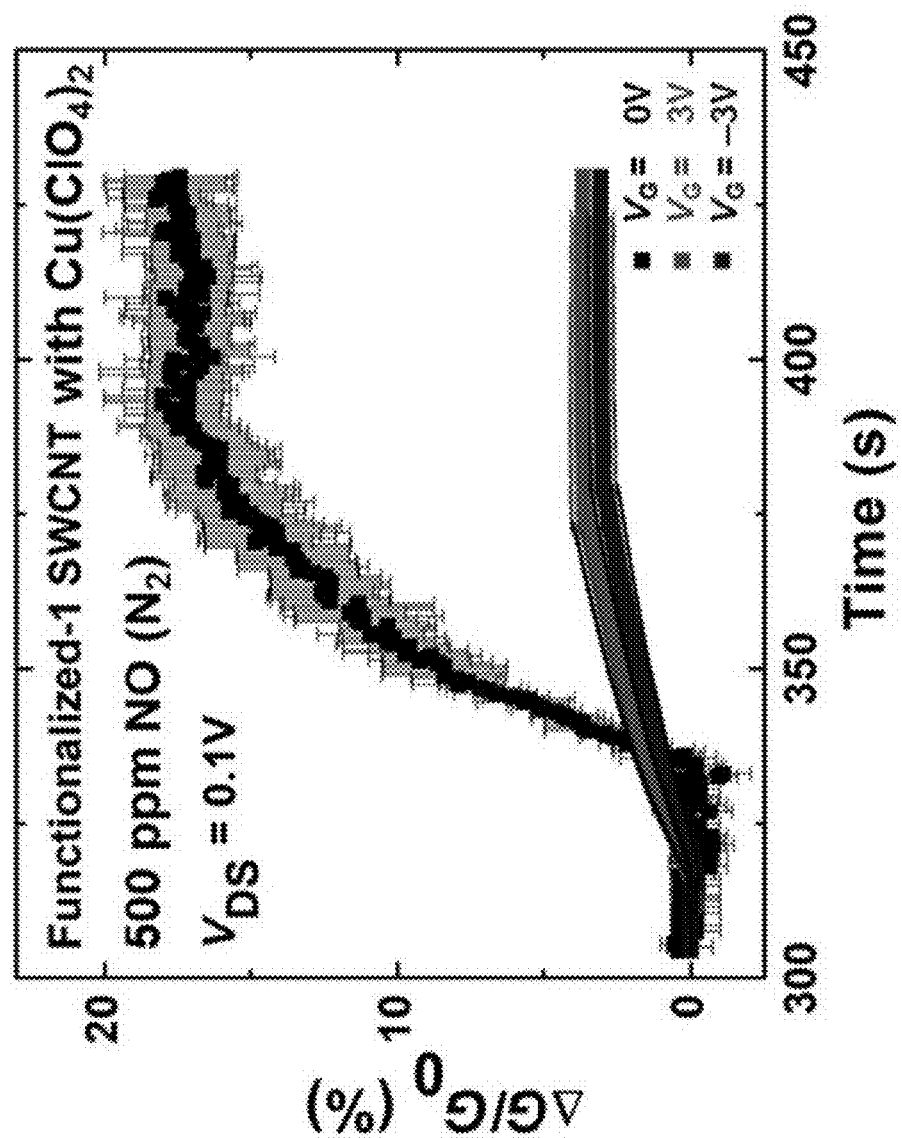
FIG. 10 depicts properties of a sensor.

Using the functionalized SWCNTs with 2-bipyridine (F-1), we then fabricated FET-based devices using copper (II) perchlorate, Cu(ClO$_4$)$_2$, as the source of copper ions. When exposed to 500 ppm of nitric oxide (NO) with nitrogen as the carrier gas, the systems comprising F-1 exhibited higher sensitivity than those with pristine SWCNTs. More interestingly, FIG. 10 shows the change in conductance of the sensors when exposed to NO with different applied gate voltages. Sensing responses at different gate voltage when exposed to 500 ppm of nitric oxide (NO). Average value and standard deviations shown from N≥6 sensors. We observed the suppression of the signals when either the positive or negative gate voltage was applied. This particular finding may provide us with a tunable way to tailor the selectivity of our sensors.

Towards Multimodal CNT-Based Sensors for the Detection of Ethylene

Figure 11:
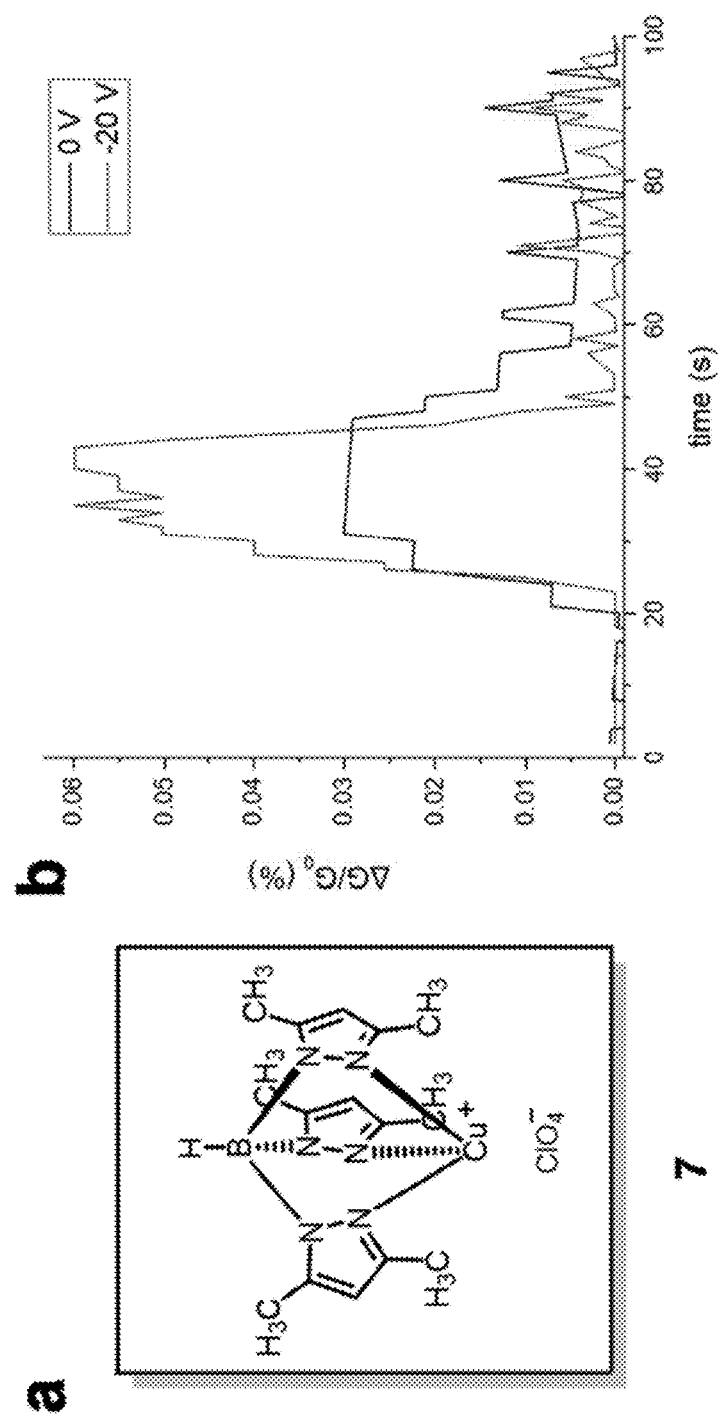
FIG. 11 depicts a sensor and properties of a sensor.

To further develop the tunability of our sensors using applied gate voltage as the switch, we aimed to create a voltage-activated sensor that can detect different analytes. Our group previously reported the detection of ethylene using a Cu(I) scorpionate complex without gate-voltage activation, however it was recently demonstrated that control over the oxidation state of the Cu(I) complex can greatly increase its performance as a selector in gas sensing schemes. See References 28A and 29A. To capitalize on this effect, we have conducted initial sensing experiments using a FET substrate to reduce all copper complexes to their Cu(I) form (Cu(I) scorpionate structure in FIG. 11). Sensors for the detection of ethylene using applied gate voltage. (a) Chemical structure of Cu(I) scorpionate complex. (b) Sensing performance using 7 at 0 V gate voltage (black curve) and at −20 V gate voltage (red curve) towards exposure of 100 ppm ethylene.

We conducted initial sensing experiments using Cu(I) scorpionate complex to investigate the influence of the gate-voltage on sensing performance. The sensors were fabricated on the FET substrates, by drop-casting dispersion of SWCNTs and the solution of the selector in sequential order. The application of gate voltage (−20 V) increased the sensing performance towards 100 ppm ethylene by 100% when compared to the same device at zero gate voltage, FIG. 11.

Preserving π-Conjugations in Functionalized SWCNTs with Aziridine Moiety

In our previous work, we discovered that the density of the pyridyl functionalization played a significant role in determining the strength of the sensing response when exposed to carbon monoxide. See Reference 30A. The pyridyl ligands improved the electronic coupling between the SWCNTs and the iron porphyrin. However, covalent functionalization also disrupted the π-conjugations along the wall of the SWCNTs. Thus, the trade-off between the density of functionalization and preserving π-conjugations led to the optimal density we observed.

Figure 12:
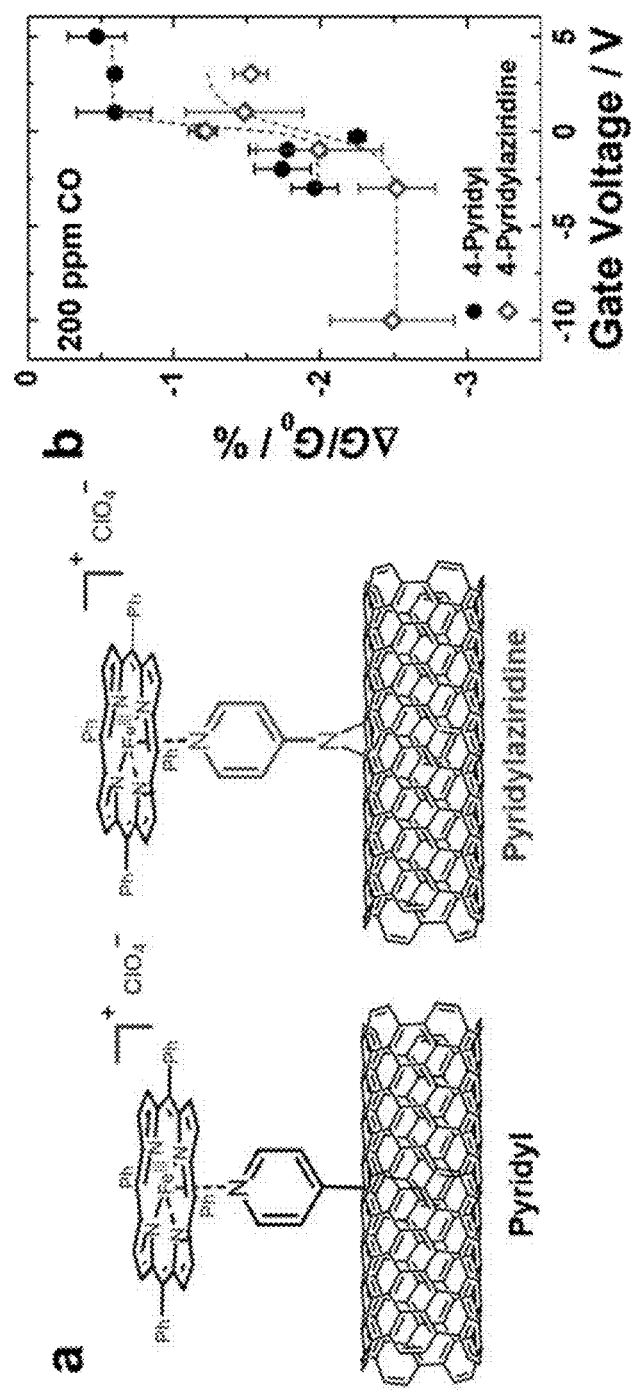
FIG. 12 depicts a sensor and properties of a sensor.

To overcome the observed competition, we have targeted the use of aziridine functionalization. The aziridine ligands maintain the it-conjugations by building the extended $sp^2$ network. The functionalization of SWCNTs through aziridination was reported by our group previously for the development of chemiresistive sensors for cyclohexanone and nitromethane. See Reference 31A. FIG. 12 shows the schematic representation of SWCNTs functionalized with pyridyl and pyridylaziridine ligands. We confirmed that the pyridylaziridine ligands were successfully functionalized through TGA and XPS. As expected, the optical and electronic properties as observed through UV-vis-NIR and Raman spectroscopy were unchanged. FIG. 12 shows the change in the conductance of the sensors when exposed to 200 ppm of CO for 2 min as a function of the applied gate voltage. FIG. 12 is a schematic representation of SWCNTs functionalized with pyridyl and pyridylaziridine and iron porphyrin for the detection of carbon monoxide (CO) and shows change in the conductance of the sensors when exposed to 200 ppm of CO for 120 s as a function of the applied gate voltage. Negative gate voltage improved the signal strength in both functionalized SWCNTs; pyridylaziridine provided larger signals than pyridyl ligand. This method of functionalization appears to be ideally suited for future application. Increasing the density of functionalization should allow for better sensitivity of the SWCNT-based sensors toward the analyte.

Towards Organic Selectors for Gate Voltage-Controlled $H_2S$ Sensors

Figure 13:
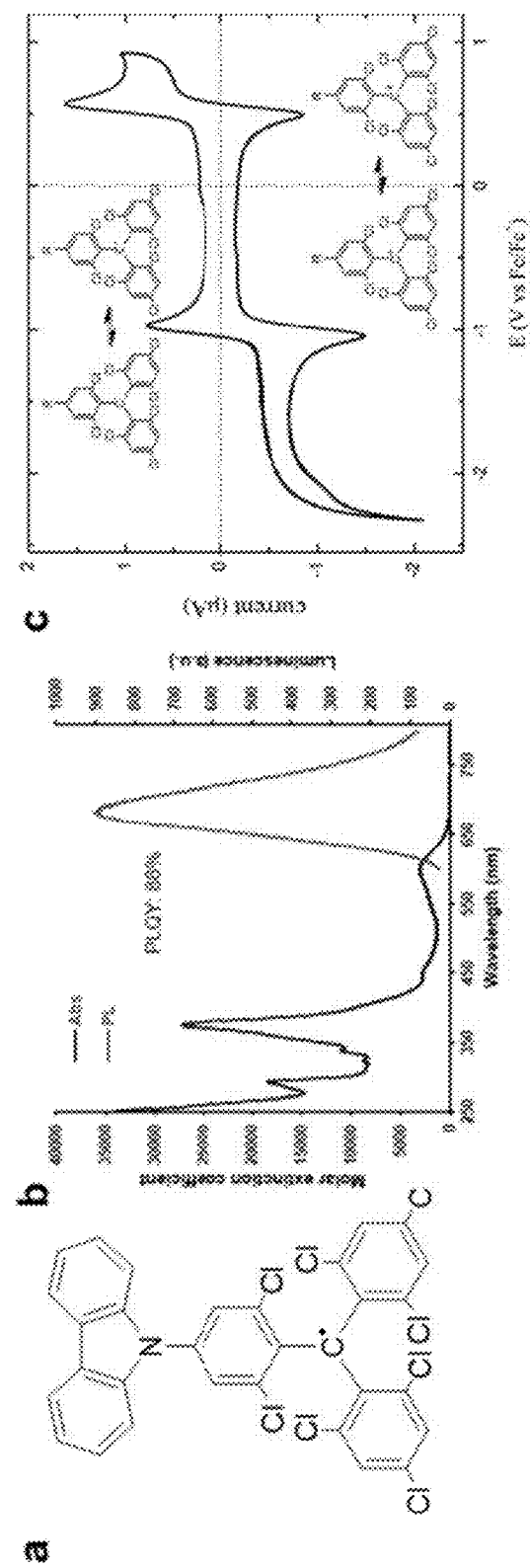
FIG. 13 depicts a sensor and properties of a sensor.

Parallel to our efforts to use metal decorated SWCNTs to develop multimodal gas sensors, we are exploring the usability of redox active organic molecules in our voltage activated sensing scheme. The advantage of using small organic molecules is (1) our ability to tune their reactivity using standard organic chemistry, (2) our ability to anchor the selector directly on the SWCNT without the need for further modification steps, and (3) the opportunity to use chemiresisitve and optical responses simultaneously to develop sensing devices with higher fidelity. We aim to sense $H_2S$, which is a highly toxic gas commonly found in the production of crude oil and gas. We designed a selector containing a stable organic radical which can be reduced and oxidized reversibly, FIG. 13. In its carbocationic form, the selector can interact favorably with $H_2S$ or $H_2S$ mimics (1-hexanethiol). FIG. 13 show chemical structure of the stable π-radical selector, absorption and emission spectrum of the selector and cyclic voltammogram of the selector in a solution of DCM with tetra-n-butylammonium fluoride electrolyte at a scan rate of 10 mV $s^{-1}$ showing two reversible redox events.

Figure 14:
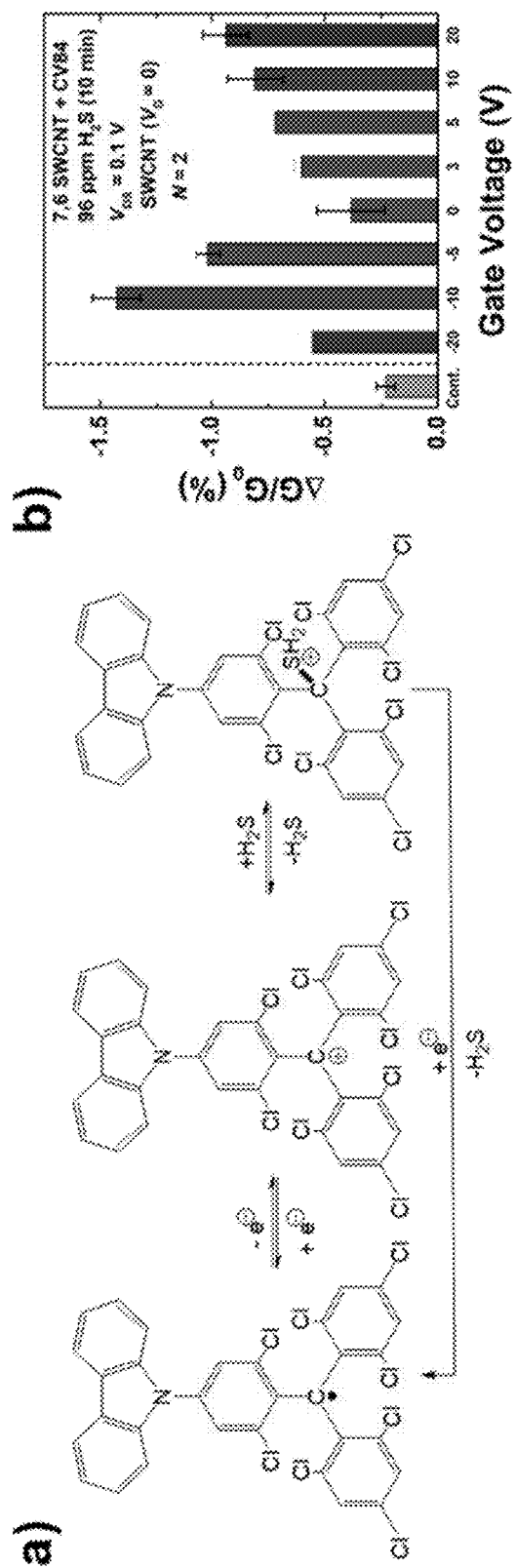
FIG. 14 depicts a sensor and properties of a sensor.

FIG. 14 show the chemical structure of the stable π-radical selector (2) and its fluorescence behavior. We first investigated the redox behavior of 2 in solution. FIG. 14 shows two reversible redox events of a solution of 2 in DCM. The oxidation and reduction of 2 can be triggered at moderate voltages (−1.00V and +0.54V vs Fc/Fc$^+$) which allows degradation-free cycling between the cationic, radical, and anionic state. The next step is the translation of the solution chemistry to the solid state where we hope to target nucleophilic, radical, and electrophilic analytes with positive, neutral, and negative gate voltages respectively.

The preliminary data showed that the selectors enhanced sensitivity towards $H_2S$. The sensors were fabricated on the FET substrates, by drop-casting dispersion of SWCNTs and the solution of the selector in sequential order. The sensors were then connected to source-meter units (Keithley 4200) with a constant applied voltage across the source and drain ($V_{DS}$) and a variable gate voltage ($V_G$). Initial experiments demonstrated that even at no applied gate voltage ($V_G$=0V) sensors comprising the selector and SWCNTs outperformed control devices with only SWCNTs. Interestingly, the application of gate voltage in both positive and negative directions improve the sensitivity towards $H_2S$. We targeted organic selectors in particular to provide reversible detection of $H_2S$, however the interaction of the current selector to $H_2S$ appears to be irreversible. Prolonged exposure resulted in an observed saturation. Due to the low reversibility and low magnitude of the response, further selector structures for the detection of $H_2S$ are explored. A chemical scheme shows how a redox-active selector can give rise to a reversible $H_2S$ sensor. Preliminary data on the changes in conductance of the composite of the organic selector and SWCNTs to the exposure of 96 ppm of $H_2S$ for 10 minutes at different applied gate voltages. The gray bar represents the response from SWCNTs without the selectors and no gate voltage The following references cited above are incorporated by reference in their entirety.

(1) Rao, A. M.; Eklund, P. C.; Bandow, S.; Thess, A.; Smalley, R. E. *Nature* 1997, 388 (6639), 257.

(2) Kong, J.; Franklin, N. R.; Zhou, C.; Chapline, M. G.; Peng, S.; Cho, K.; Dai, H. *Science* 2000, 287 (5453), 622.
(3) Hangarter, C. M.; Chartuprayoon, N.; Hernandez, S. C.; Choa, Y.; Myung, N. V. *Nano Today* 2013, 8 (1), 39.
(4) Jurs, P. C.; Bakken, G. A.; McClelland, H. E. *Chem. Rev.* 2000, 100 (7), 2649.
(5) Wang, J.-F.; Chou, K.-C. *PLoS One* 2011, 6 (4), e18414.
(6) Savagatrup, S.; Schroeder, V.; He, X.; Lin, S.; He, M.; Yassine, O.; Salama, K. N.; Zhang, X.; Swager, T. M. *Angew. Chemie Int. Ed.* 2017, 56 (45), 14066.
(7) Ishihara, S.; O'Kelly, C. J.; Tanaka, T.; Kataura, H.; Labuta, J.; Shingaya, Y.; Nakayama, T.; Ohsawa, T.; Nakanishi, T.; Swager, T. M. *ACS Appl. Mater. Interfaces* 2017, 9 (43), 38062.
(8) Star, A.; Joshi, V.; Skarupo, S.; Thomas, D.; Gabriel, J. C. P. *J. Phys. Chem. B* 2006, 110 (42), 21014.
(9) Wang, J.; Timchalk, C.; Lin, Y. *Environ. Sci. Technol.* 2008, 42 (7), 2688.
(10) Tang, X.; Bansaruntip, S.; Nakayama, N.; Yenilmez, E.; Chang, Y. I.; Wang, Q. *Nano Lett.* 2006, 6 (8), 1632.
(11) Weizmann, Y.; Chenoweth, D. M.; Swager, T. M. *J. Am. Chem. Soc.* 2011, 133 (10), 3238.
(12) Swager, T. M.; Azzarell, J. M.; White, K. R. Selective detection of alkenes or alkynes US20160169810A1, Apr. 4 2014.
(13) Azzarelli, J. M. Wirelessly addressable chemiresistors: carbon nanotube-based chemical sensors and dosimeters, Massachusetts Institute of Technology, June 2016.
(14) Zheng, C.; Wang, D.; Stahl, S. S. *J. Am. Chem. Soc.* 2012, 134 (40), 16496.
(15) Andappan, M. M. S.; Nilsson, P.; Larhed, M. *Chem. Commun.* 2004, 2 (2), 218.
(16) Enquist, P.-A.; Lindh, J.; Nilsson, P.; Larhed, M. *Green Chem.* 2006, 8 (4), 338.
(17) Zheng, C.; Stahl, S. *Chem. Commun.* 2015, 51, 12771.
(18) OSHA. Chemical Sampling—Ethyl Acrylate, Methyl Acrylate—Method 92 retreived from https://www.osha.gov/dts/sltc/methods/organic/org092/org092.html on January 2018.
(19) Hideji, T.; Kazuo, H. *Toxicol. Lett.* 1982, 11 (1-2), 125.
(20) Autian, J. *Environ. Health Perspect.* 1975, 11 (June), 141.
(21) Ghanayem, B. I.; Maronpot, R. R.; Matthews, H. B. *Toxicol. Appl. Pharmacol.* 1986, 83 (3), 576.
(22) Moore, M. M.; Amtower, A.; Doerr, C. L.; Brock, K. H.; Dearfield, K. L. *Environ. Mol. Mutagen.* 1988, 11 (1), 49.
(23) Zhu, R.; Azzarelli, J. M.; Swager, T. M. *Angew. Chemie—Int. Ed.* 2016, 55 (33), 9662.
(24) Ishihara, S.; Azzarelli, J. M.; Krikorian, M.; Swager, T. M. *J. Am. Chem. Soc.* 2016, 138 (26), 8221.
(25) Gerritsma, D. A.; Robertson, A.; McNulty, J.; Capretta, A. *Tetrahedron Lett.* 2004, 45, 7629.
(26) Reetz, M.; de Vries, J. *Chem. Commun.* 2004, No. 14, 1559.
(27) Spekreijse, J.; Le Notre, J.; van Haveren, J.; Scott, E. L.; Sanders, J. P. M. *Green Chem.* 2012, 14 (10), 2747.
(28) Izawa, Y.; Zheng, C.; Stahl, S. S. *Angew. Chemie Int. Ed.* 2013, 52 (13), 3672.
(29) Collins, P. G.; Bradley, K.; Ishigami, M.; Zettl, A. *Science* 2007, 287 (March), 1801.
(30) Kang, D.; Park, N.; Ko, J.; Bae, E.; Park, W. *Nanotechnology* 2005, 16 (8), 1048.
(31) Reetz, M. T.; Westermann, E.; Lohmer, R.; Lohmer, G. *Tetrahedron Lett.* 1998, 39 (46), 8449.
(32) De Vries, A. H. M.; Parlevliet, F. J.; Schmieder-van De Vondervoort, L.; Mommers, J. H. M.; Henderickx, H. J. W.; Walet, M. A. M.; De Vries, J. G. *Adv. Synth. Catal.* 2002, 344 (9), 996.
(33) OSHA. Occupational Safety and Health Standards. 1910.1000 TABLE Z-1, 1993.
(34) Mariampillai, B.; Alliot, J.; Li, M.; Lautens, M. *J. Am. Chem. Soc.* 2007, 129 (49), 15372.
(35) Weinstabl, H.; Suhartono, M.; Qureshi, Z.; Lautens, M. *Angew. Chemie—Int. Ed.* 2013, 52 (20), 5305.
(36) Catellani, M.; Motti, E.; Ca, N. Della. *Acc. Chem. Res.* 2008, 41 (11), 1512.
(37) Jiao, L.; Herdtweck, E.; Bach, T. *J. Am. Chem. Soc.* 2012, 134 (35), 14563.
(38) Pu, X.; Li, H.; Colacot, T. J. *J. Org. Chem.* 2013, 78 (2), 568.
(1A) Swager, T. M., Savagatrup, S., Schröder, V., He, X., Lin, S., He, M., Yassine, O., Salama, K. N. and Zhang, X. X. Sensors Including Redox-Active Metal Complexes. U.S. Patent Application No. 62/560,186.
(2A) Schroeder, V.; Savagatrup, S.; He, M.; Lin, S.; Swager, T. M. Carbon Nanotube Chemical Sensors. *Chem. Rev.* 2018.
(3A) Que, L.; Tolman, W. B. Biologically Inspired Oxidation Catalysis. *Nature* 2008, 455 (7211), 333-340.
(4A) Tolman, W. B. Editorial for the Virtual Issue on Models of Metalloenzymes. *Inorg. Chem.* 2013, 52 (13), 7307-7310.
(5A) De La Torre, M. C.; Siena, M. A. Comments on Recent Achievements in Biomimetic Organic Synthesis. *Angew. Chemie—Int. Ed.* 2003, 43 (2), 160-181.
(6A) Lippard, S. J.; Berg, J. M. *Principles of Bioinorganic Chemistry;* University Science Books: Mill Valey, Calif., 1994.
(7A) He, Y.; Zhang, J.; Zhao, J. Electron Transport and CO Sensing Characteristics of Fe(II) Porphyrin with Single-Walled Carbon Nanotube Electrodes. *J. Phys. Chem. C* 2014, 118 (32), 18325-18333.
(8A) Shimizu, T.; Huang, D.; Yan, F.; Stranava, M.; Bartosova, M.; Fojtikova, V.; Martinková, M. Gaseous $O_2$, NO, and CO in Signal Transduction: Structure and Function Relationships of Heme-Based Gas Sensors and Heme-Redox Sensors. *Chem. Rev.* 2015, 115 (13), 6491-6533.
(9A) He, M.; Swager, T. M. Covalent Functionalization of Carbon Nanomaterials with Iodonium Salts. *Chem. Mater.* 2016, 28 (23), 8542-8549.
(10A) Santucci, S.; Picozzi, S.; Di Gregorio, F.; Lozzi, L.; Cantalini, C.; Valentini, L.; Kenny, J. M.; Delley, B. NO2 and CO Gas Adsorption on Carbon Nanotubes: Experiment and Theory. *J. Chem. Phys.* 2003, 119 (20), 10904-10910.
(11A) Fu, D.; Lim, H.; Shi, Y.; Dong, X.; Mhaisalkar, S. G.; Chen, Y.; Moochhala, S.; Li, L. Differentiation of Gas Molecules Using Flexible and All-Carbon Nanotube Devices. *J. Phys. Chem. C* 2008, 112 (3), 650-653.
(12A) Kauffman, D. R.; Star, A. Carbon Nanotube Gas and Vapor Sensors. *Angew. Chem. Int. Ed. Engl.* 2008, 47 (35), 6550-6570.
(13A) Liu, S. F.; Lin, S.; Swager, T. M. An Organocobalt-Carbon Nanotube Chemiresistive Carbon Monoxide Detector. *ACS Sensors* 2016, 1 (4), 354-357.

(14A) Paul, S.; Amalraj, F.; Radhakrishnan, S. CO Sensor Based on Polypyrrole Functionalized with Iron Porphyrin. *Synth. Met.* 2009, 159 (11), 1019-1023.

(15A) Maser, W.; Benito, E. M.; Munoz, E.; Martinez, M. T. *Functionalized Nanoscale Materials, Devices and Systems;* A. Vaseashta, I. N. M., Ed.; Springer: Dordrecht, 2008.

(16A) Banerjee, S.; Hemraj-Benny, T.; Wong, S. S. Covalent Surface Chemistry of Single-Walled Carbon Nanotubes. *Adv. Mater.* 2005, 17 (1), 17-29.

(17A) Liu, L.; Etika, K. C.; Liao, K. S.; Hess, L. A.; Bergbreiter, D. E.; Grunlan, J. C. Comparison of Covalently and Noncovalently Functionalized Carbon Nanotubes in Epoxy. *Macromol. Rapid Commun.* 2009, 30 (8), 627-632.

(18A) Occupational Safety and Health Administration. Carbon Monoxide In Workplace Atmospheres (Direct-Reading Monitor).

(19A) Rovira, C.; Ballone, P.; Parrinello, M. A Density Functional Study of Iron-Porphyrin Complexes. *Chem. Phys. Lett.* 1997, 271 (June), 247-250.

(20A) Blomberg, L. M.; Blomberg, M. R. A.; Siegbahn, P. E. M. A Theoretical Study on the Binding of O2, NO and CO to Heme Proteins. *J. Inorg. Biochem.* 2005, 99 (4), 949-958.

(21A) Abdurahman, A.; Renger, T. Density Functional Studies of Iron-Porphyrin Cation with Small Ligands X (X: O, CO, NO, O2, N2, H2O, N2O, CO2). *J. Phys. Chem. A* 2009, 113 (32), 9202-9206.

(22A) Zanolli, Z.; Leghrib, R.; Felten, A.; Pireaux, J.-J. J.; Llobet, E.; Charlier, J.-C. C. Gas Sensing with Au-Decorated Carbon Nanotubes. *ACS Nano* 2011, 5 (6), 4592-4599.

(23A) Wang, Q.; Tong, Y.; Xu, X. A Theoretical Study of the Binding Mechanisms of Atomic Platinum on Be-, B-, N-, O-Doped (6,6) Single-Walled Carbon Nanotubes. *Struct. Chem.* 2015, 26 (3), 815-822.

(24A) Yim, W. L.; Liu, Z. F. A Reexamination of the Chemisorption and Desorption of Ozone on the Exterior of a (5,5) Single-Walled Carbon Nanotube. *Chem. Phys. Lett.* 2004, 398, 297-303.

(25A) Penza, M.; Alvisi, M.; Rossi, R.; Serra, E.; Paolesse, R.; D'Amico, A.; Di Natale, C. Carbon Nanotube Films as a Platform to Transduce Molecular Recognition Events in Metalloporphyrins. *Nanotechnology* 2011, 22 (12), 125502.

(26A) Kauffman, D. R.; Kuzmych, O.; Star, A. Interactions between Single-Walled Carbon Nanotubes and Tetraphenyl Metalloporphyrins: Correlation between Spectroscopic and FET Measurements. *J. Phys. Chem. C* 2007, 111 (9), 3539-3543.

(27A) Liu, S. F.; Petty, A. R.; Sazama, G. T.; Swager, T. M. Single-Walled Carbon Nanotube/Metalloporphyrin Composites for the Chemiresistive Detection of Amines and Meat Spoilage. *Angew. Chemie Int. Ed.* 2015, 54 (22), 6554-6557.

(28A) Esser, B.; Schnorr, J. M.; Swager, T. M. Selective Detection of Ethylene Gas Using Carbon Nanotube-Based Devices: Utility in Determination of Fruit Ripeness. *Angew. Chemie—Int. Ed.* 2012, 51 (23), 5752-5756.

(29A) Fu, W.; Van Dijkman, T. F.; Lima, L. M. C.; Jiang, F.; Schneider, G. F.; Bouwman, E. Ultrasensitive Ethene Detector Based on a Graphene-Copper(I) Hybrid Material. *Nano Lett.* 2017, 17 (12), 7980-7988.

(30A) Savagatrup, S.; Schroeder, V.; He, X.; Lin, S.; He, M.; Yassine, O.; Salama, K. N.; Zhang, X.-X.; Swager, T. M. Bio-Inspired Carbon Monoxide Sensors with Voltage-Activated Sensitivity. *Angew. Chemie Int. Ed.* 2017, 56 (45), 14066-14070.

(31A) Schnorr, J. M.; van der Zwaag, D.; Walish, J. J.; Weizmann, Y.; Swager, T. M. Sensory Arrays of Covalently Functionalized Single-Walled Carbon Nanotubes for Explosive Detection. *Adv. Funct. Mater.* 2013, 23 (42), 5285-5291.

(32A) Murat, A.; Rungger, I.; Sanvito, S.; Schwingenschlögl, U. Mechanism of H 2 O-Induced Conductance Changes in AuCl 4-Functionalized CNTs. *J. Phys. Chem. C* 2015, 119 (17), 9568-9573.

(33A) Bushmaker, A. W.; Oklejas, V.; Walker, D.; Hopkins, A. R.; Chen, J.; Cronin, S. B. Single-Ion Adsorption and Switching in Carbon Nanotubes. *Nat. Commun.* 2016, 7, 10475.

(34A) Liu, S. F.; Moh, L. C. H.; Swager, T. M. Single-Walled Carbon Nanotube-Metalloporphyrin Chemiresistive Gas Sensor Arrays for Volatile Organic Compounds. *Chem. Mater.* 2015, 27 (10), 3560-3563.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A sensor comprising:
    a conductive region in electrical communication with at least two electrodes, the conductive region including a conductive material and a catalytic mixture that catalyzes conversion of an analyte to an isolatable product.

2. The sensor of claim 1, wherein the conductive material includes a carbon material.

3. The sensor of claim 2, wherein the carbon material includes amorphous carbon, graphene, graphite, a single walled carbon nanotube, or a multiwalled carbon nanotube.

4. The sensor of claim 1, wherein the conductive material is a conductive polymer.

5. The sensor of claim 1, wherein the analyte is an alkene.

6. The sensor of claim 5, wherein the catalytic mixture includes a catalytic metal complex.

7. The sensor of claim 6, wherein the catalytic mixture includes reactant that reacts with the analyte in the presence of the catalyst.

8. The sensor of claim 1, wherein the analyte includes an acrylate.

9. The sensor of claim 1, further comprising a selector.

10. The sensor of claim 9, wherein the selector includes an aromatic, heteroaromatic, polyaromatic or metal complex.

11. A method of sensing an analyte, comprising:
    exposing a sensor to a sample, the sensor including:
        a conductive region in electrical communication with at least two electrodes, the conductive region including a conductive material and a catalytic mixture that catalyzes conversion of an analyte in the sample to an isolatable product; and
    measuring an electrical property at the electrodes.

12. The method of claim 11, wherein the sample includes a volatile organic molecule.

13. The method of claim 11, wherein the conductive material includes a carbon material.

14. The method of claim 13, wherein the carbon material includes amorphous carbon, graphene, graphite, a single walled carbon nanotube, or a multiwalled carbon nanotube.

15. The method of claim 11, wherein the conductive material is a conductive polymer.

16. The method of claim 11, wherein the analyte is an alkene.

17. The method of claim 16, wherein the catalytic mixture includes a catalytic metal complex.

18. The method of claim 17, wherein the catalytic mixture includes reactant that reacts with the analyte in the presence of the catalyst.

19. The method of claim 11, wherein the analyte includes an acrylate.

20. A method of preparing a sensor comprising:
   forming a conductive region in electrical communication with at least two electrodes, the conductive region including a conductive material and a catalytic mixture that catalyzes conversion of an analyte to an isolatable product.

\* \* \* \* \*